(12) United States Patent
DeLuca et al.

(10) Patent No.: US 8,158,117 B2
(45) Date of Patent: *Apr. 17, 2012

(54) METHODS AND COMPOSITIONS FOR PHOSPHATE BINDING

(75) Inventors: Hector F. DeLuca, Deerfield, WI (US); Katie Beth Williams, Madison, WI (US); Katarzyna Barcyka, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1032 days.

This patent is subject to a terminal disclaimer.

(21) Appl. No.: 11/520,389

(22) Filed: Sep. 13, 2006

(65) Prior Publication Data

US 2007/0071715 A1   Mar. 29, 2007

Related U.S. Application Data

(60) Provisional application No. 60/717,072, filed on Sep. 14, 2005.

(51) Int. Cl.
*A61K 31/785* (2006.01)
*A61K 31/13* (2006.01)
*A01N 33/02* (2006.01)
*A01N 33/18* (2006.01)

(52) U.S. Cl. ............... 424/78.12; 514/663; 514/740; 977/734; 977/754

(58) Field of Classification Search ............... 424/78.27, 424/78.12; 525/540; 977/734, 754; 514/663, 514/740

See application file for complete search history.

(56) References Cited

U.S. PATENT DOCUMENTS

| | | | |
|---|---|---|---|
| 4,871,779 A | 10/1989 | Killat et al. | |
| 5,530,092 A | 6/1996 | Meijer et al. | |
| 5,610,268 A | 3/1997 | Meijer et al. | |
| 5,698,662 A | 12/1997 | Stoelwinder et al. | |
| 5,788,989 A | 8/1998 | Jansen et al. | |
| 6,156,873 A * | 12/2000 | Krause et al. ............ | 528/395 |
| 6,262,257 B1 * | 7/2001 | Gale et al. ............... | 540/145 |
| 6,726,905 B1 * | 4/2004 | Mandeville et al. ....... | 424/78.35 |
| 7,470,369 B2 * | 12/2008 | Diallo ..................... | 210/650 |
| 2004/0040554 A1 * | 3/2004 | Matsuoka et al. ........ | 127/30 |
| 2005/0019923 A1 | 1/2005 | Uchegbu et al. | |
| 2005/0147580 A1 | 7/2005 | Connor et al. | |
| 2006/0204472 A1 * | 9/2006 | Paleos et al. ............ | 424/78.27 |
| 2007/0110706 A1 * | 5/2007 | Connor et al. ........... | 424/78.12 |

FOREIGN PATENT DOCUMENTS

WO  WO 2005/041902 A2  12/2005
WO  2008/011047 A2  1/2008

OTHER PUBLICATIONS

Daniel et al., J. Am. Chem. Soc., 2003, 125, p. 1150-1151.*
Kabanov et al., Macromolecules, 1999, 32, p. 1904-1909.*
de Brabander-van den Berg, E. et al., Angew. Chem. Int. Ed., 1993, 32(9), p. 1308-1311.*
Klajnert, B. et al., Acta Biochimica Polonica, 2001, 48(1), p. 199-208.*
Zimmer, A et al: "Complex formation of Ni(II), Cu(II), Pd (II), and Co (III) with 1,2,3,4-tetraaminobutane." Chemistry 2001, vol. 7, 4:917-931, XP009076062.
Bachmann, F et al: "Synthesis of novel polyurethanes . . . " Macromolecular Chemistry and Physics, 202 (17), 3410-3419 coden: Mchpes; Issn: 1022-1352, 2001, Scheme 1.
Covassin, L et al: "Synthesis of spermidine . . . " Bioorganic & Medicinal Chemisry Letters, Oxford, GB, vol. 9, No. 12, Jun. 21, 1999, 1709-1714 XP004167745.
Johan, F.G., "Journal of the American Chemical Society," Apr. 1995, vol. 117, No. 15, pp. 4417-4418.

* cited by examiner

*Primary Examiner* — Michael G Hartley
*Assistant Examiner* — Leah Schlientz
(74) *Attorney, Agent, or Firm* — Quarles & Brady LLP

(57) ABSTRACT

The present invention provides improved methods and compositions for therapeutically controlling and/or reducing serum phosphate levels in animals and mammalian patients. The methods comprise administering to the patient an amount of a dendrimer composition effective to prevent absorption of substantial amounts of phosphate from the patient's GI tract. In a preferred version, a dose of between 2.5 and 15 grams per day is effective to prevent over 80% of phosphate present in the patient's GI tract from being absorbed. The dendrimer composition may comprise a hydrochloride, hydrobromide, hydroacetate or hydroanionic form.

6 Claims, 15 Drawing Sheets

Structure 1

Structure 2

Structure 3

Structure 4

Structure 5

Structure 6

**Structure 7

7
DAB-Am-8 Dendrimer
Generation 2.0

8

9
DAB-Am-16 Dendrimer
Generation 3.0

10

US 8,158,117 B2

METHODS AND COMPOSITIONS FOR PHOSPHATE BINDING

CROSS-REFERENCE TO RELATED APPLICATIONS

This application claims priority to U.S. provisional application No. 60/717,072, filed Sep. 14, 2005, which is hereby incorporated by reference herein.

STATEMENT REGARDING FEDERALLY SPONSORED RESEARCH OR DEVELOPMENT

Not Applicable.

FIELD OF THE INVENTION

The invention relates generally to methods and compositions for therapeutic phosphate binding in a mammalian patient, preferably by use of dendrimers, as defined below. Most preferably, the methods and compositions of the present invention are used with dialysis patients and others who have an inability to excrete phosphate.

BACKGROUND

The kidney is essential not only for its ability to filter toxins and excess nutrients from the blood, but also for its ability to synthesize the active form of vitamin $D_3$, 1,25-dihydroxyvitamin $D_3$ [$1,25(OH)_2D_3$]. In patients with chronic kidney disease, both these functions are impaired. Consequently, levels of $1,25(OH)_2D_3$ decline, leading to hypocalcemia. Meanwhile, nutrients, particularly phosphorus, accumulate in the blood. Hypocalcemia and hyperphosphatemia are both potent stimulators of parathyroid hormone (PTH) secretion. Over time, hyperparathyroidism in the presence of even trace amounts of $1,25(OH)_2D_3$ cause excess bone resorption, leading to a condition known as renal osteodystrophy (1). In addition to dialysis treatment, it is essential to suppress excessive PTH levels and reduce phosphorus in the blood to prevent this condition.

Vitamin D analogs, such as 1,25-dihydroxy-19-nor-vitamin $D_2$ (19-nor-$D_2$, Zemplar®, Abbott Laboratories, Abbott Park, Ill.) and 1 α-hydroxyvitamin $D_2$ [$1\alpha$-(OH)$D_2$, Hectorol®, Genzyme Corporation/Bone Care International, Middleton, WIS.] are administered to patients to suppress hyperparathyroidism. Although these analogs are effective at suppressing PTH levels, they still retain some ability to stimulate intestinal calcium and phosphate absorption, which may be problematic when the analogs are administered at high doses or in conjunction with calcium-based oral phosphate binders (1).

Reducing the absorption of phosphorus from foods is also a challenging task. The current Recommended Dietary Allowance (RDA) for phosphorus is 700 mg per day (2), but most Americans consume 1000-1600 mg of phosphorus each day (3). Dietary phosphorus restriction is not very effective due to the richness of phosphorus in foods such as dairy products, meat, fish, eggs, nuts, grains, baked goods, and soft drinks. Moreover, it is estimated that 65-75% of consumed phosphorus is absorbed (4). As a result, oral phosphate binders are often administered with meals to reduce the absorption of phosphorus.

In the 1970s, aluminum-based binders were extensively used to bind phosphate from foods, but the use was severely reduced after aluminum was shown to accumulate in patients causing toxic side-effects such as bone disease, encephalopathy, and anemia (5). Calcium acetate (PhosLo, Nabi Pharmaceuticals, Boca Raton, Fla.) was then developed as an alternative to aluminum-based binders, but must be administered at high levels to be effective. Furthermore, when administered in conjunction with $1,25(OH)_2D_3$ or a vitamin D analog, the oral calcium may contribute to hypercalcemia (5). Recently, lanthanum carbonate (Fosrenol®, Shire US Incorporated, Wayne, Pa.) was approved by the FDA for use as an oral phosphate binder. Although effective, its low rate of absorption raises some speculation that toxicity issues may arise with long-term use (6).

Sevelamer hydrochloride (Renagel®, Genzyme Corporation, Cambridge, Mass.), a phosphate-binding polymer, has been successfully used to reduce absorption of dietary phosphorus with fewer side effects than aluminum or calcium (7). Unfortunately, sevelamer hydrochloride is costly (average cost of $4400 per year in 2002) and must be taken in large quantities (average dose of 6.5 g per day) to be effective (8).

Dendrimers are well known therapeutic tools. Dendrimers have been used in applications including imaging agents, nano-scaffolds, antitumor drugs, gene transfection agents, nanoscale containers and biomimetic artificial proteins (14). However, therapeutic dendrimer compositions that bind phosphate, thereby treating hypocalcemia, hyperphosphatemia and chronic kidney disease, are not known.

Thus, a need exists for dendrimeric compositions containing varying amounts of free amines that can bind phosphate and inhibit its absorption in vivo.

BRIEF DESCRIPTION OF THE INVENTION

The present invention provides an improved method of controlling serum phosphate levels in mammals comprising administering to the mammal an amount of a dendrimer composition effective to prevent absorption of substantial amounts of phosphate from the mammal's GI tract, wherein the mammal's serum phosphate level is controlled. A dose of between 2.5 and 15 grams per day is effective to prevent at least 50% of phosphate present in the mammal's GI tract from being absorbed. In a preferred version at least 80% of the phosphate is prevented from being absorbed. The dendrimer composition may comprise a hydrochloride, hydrobromide, hydroacetate, or some hydro anion form.

In a preferred version the dendrimer is selected from the group consisting of erythro-1,2,3,4-tetraaminobutane tetrahydrochloride or diaminobutane. In a further preferred version the dendrimer composition comprises a dendrimer according to Structures 4, 5 or 6 (FIGS. 1D-1F).

In another version, the present invention provides a method of reducing intestinal phosphate absorption in animals by administering to the animal an amount of a dendrimer composition effective to prevent absorption of substantial amounts of phosphate from the animal's GI tract, wherein the animals serum phosphate level is reduced. In a preferred version, a daily dose of between 2.5 and 15 grams per day is effective to prevent at least 50% of phosphate present in the animal's GI tract from being absorbed. In a preferred version at least 80% of the phosphate is prevented from being absorbed. The dendrimer composition may comprise a hydrochloride, hydrobromide or hydroacetate or other hydroanionic forms.

BRIEF DESCRIPTION OF THE FIGURES

FIG. 1 shows therapeutic phosphate binders of the present invention.

Structure 2: erythro-1,2,3,4-tetraaminobutane tetrahydrochloride (KB-54).

FIG. 2A) Percent of oral $^{33}$P dose remaining in the digestive tract. *Significantly different from rats administered water prior to $^{33}$P in same level of unlabeled phosphate (p<0.05). **Significantly different from rats administered 14.4 mg Renagel® prior to $^{33}$P in same level of unlabeled phosphate (p<0.05). FIG. 2B) Percent of oral $^{33}$P dose detected in serum. *Significantly different from rats administered water prior to $^{33}$P in same level of unlabeled phosphate (p<0.05).

FIG. 3A) Percent of oral $^{33}$P dose remaining in the digestive tract. FIG. 3B) Percent of oral $^{33}$P dose detected in serum. *Significantly different from rats administered water prior to $^{33}$P (p<0.05). **Significantly different from rats administered Renagel® prior to $^{33}$P (p<0.05).

FIG. 4A) Percent of oral $^{33}$P dose remaining in the digestive tract. FIG. 4B) Percent of oral $^{33}$P dose detected in serum. *Significantly different from rats administered water prior to $^{33}$P (p<0.05). **Significantly different from rats administered Renagel® prior to $^{33}$P (p<0.05).

FIG. 5A) Percent of oral $^{33}$P dose remaining in the digestive tract. FIG. 5B) Percent of oral $^{33}$P dose detected in serum. *Significantly different from rats administered water prior to $^{33}$P (p<0.05). **Significantly different from rats administered Renagel® prior to $^{33}$P (p<0.05). ND = none detectable.

DETAILED DESCRIPTION OF THE INVENTION

The present invention provides an improved method of therapeutic phosphate binding in an animal or mammalian patient, preferably by use of a dendrimer, as defined below. Most preferably, the method of present invention is used with dialysis patients and others who have an inability to excrete phosphate.

Figure 1A:
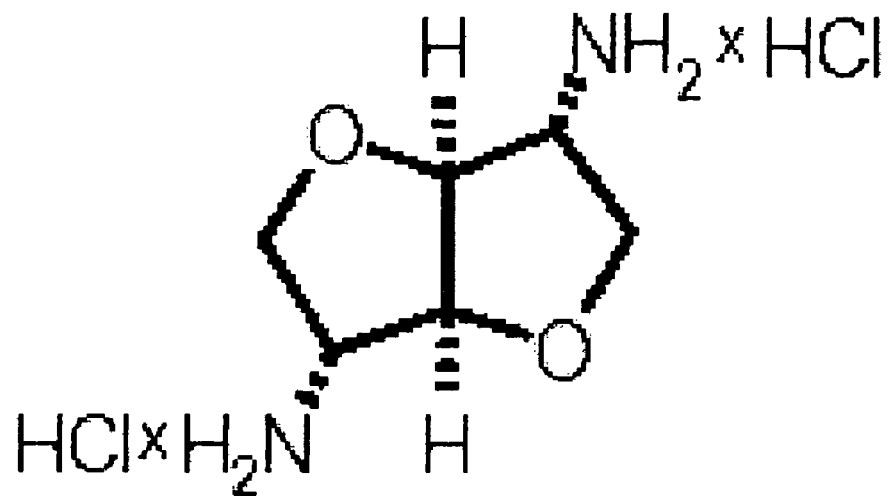
FIG. 1A) Structure 1: 1,4:3,6-Dianhydro-2,5-diamino-2,5-dideoxy-D-iditol dihydrochloride (FC).
Figure 1B:
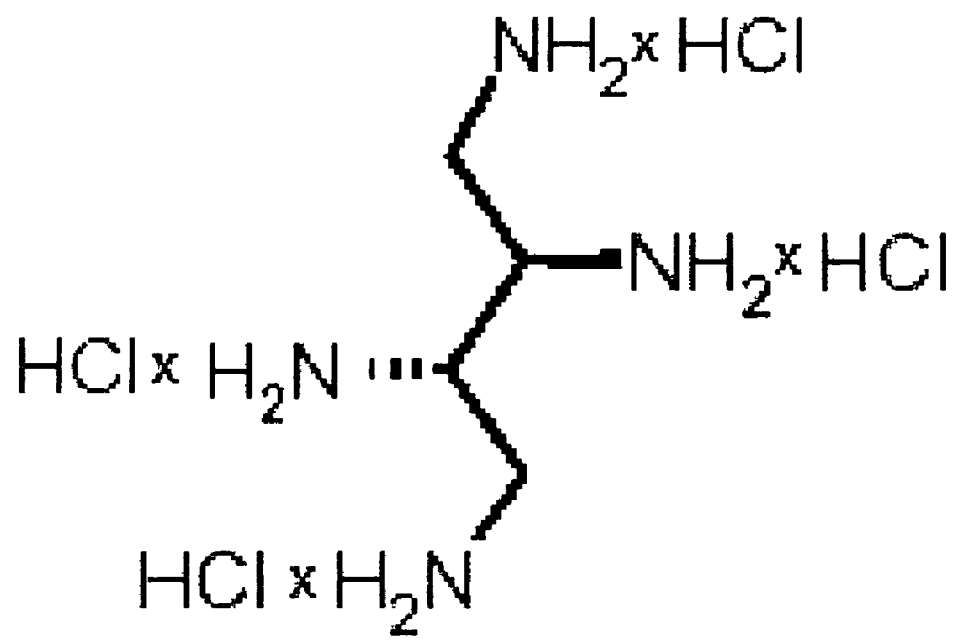
FIG. 1B)
Figure 1C:
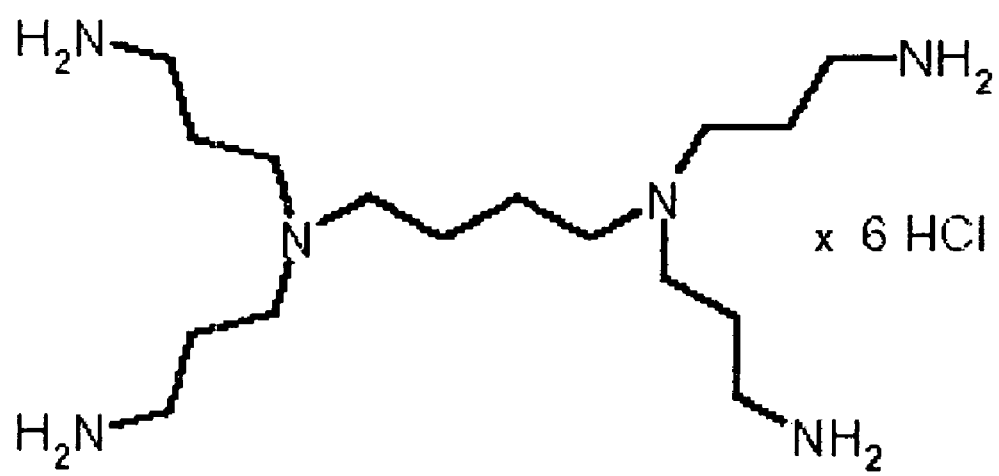
FIG. 1C) Structure 3: Diaminobutane dendrimer Generation 1 (DAB4-Cl).
Figure 1D:
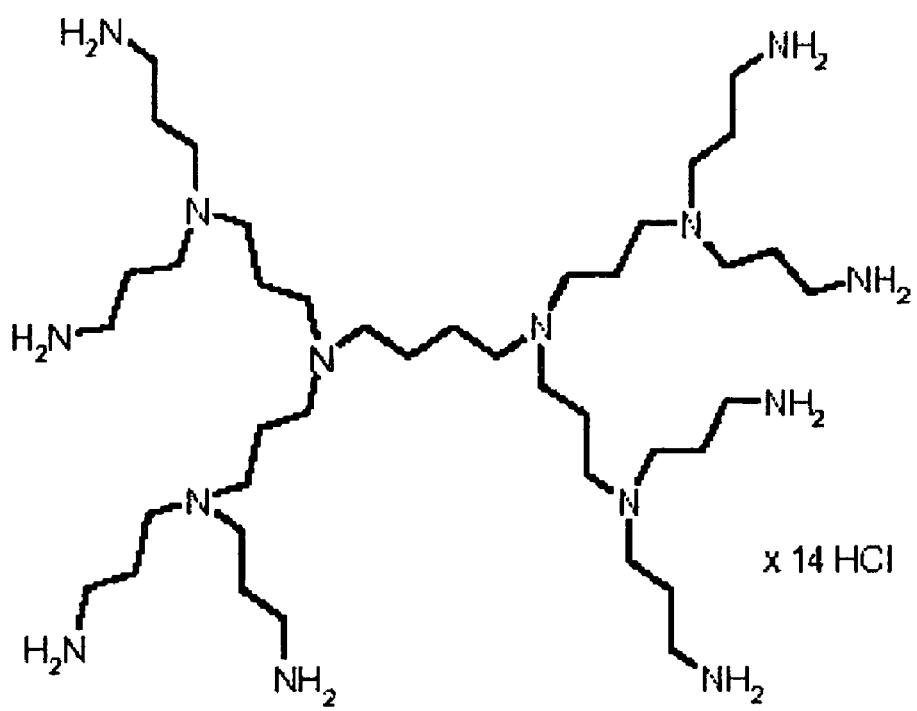
FIG. 1D) Structure 4: Diaminobutane dendrimer Generation 2 (DAB-8-Cl).
Figure 1E:
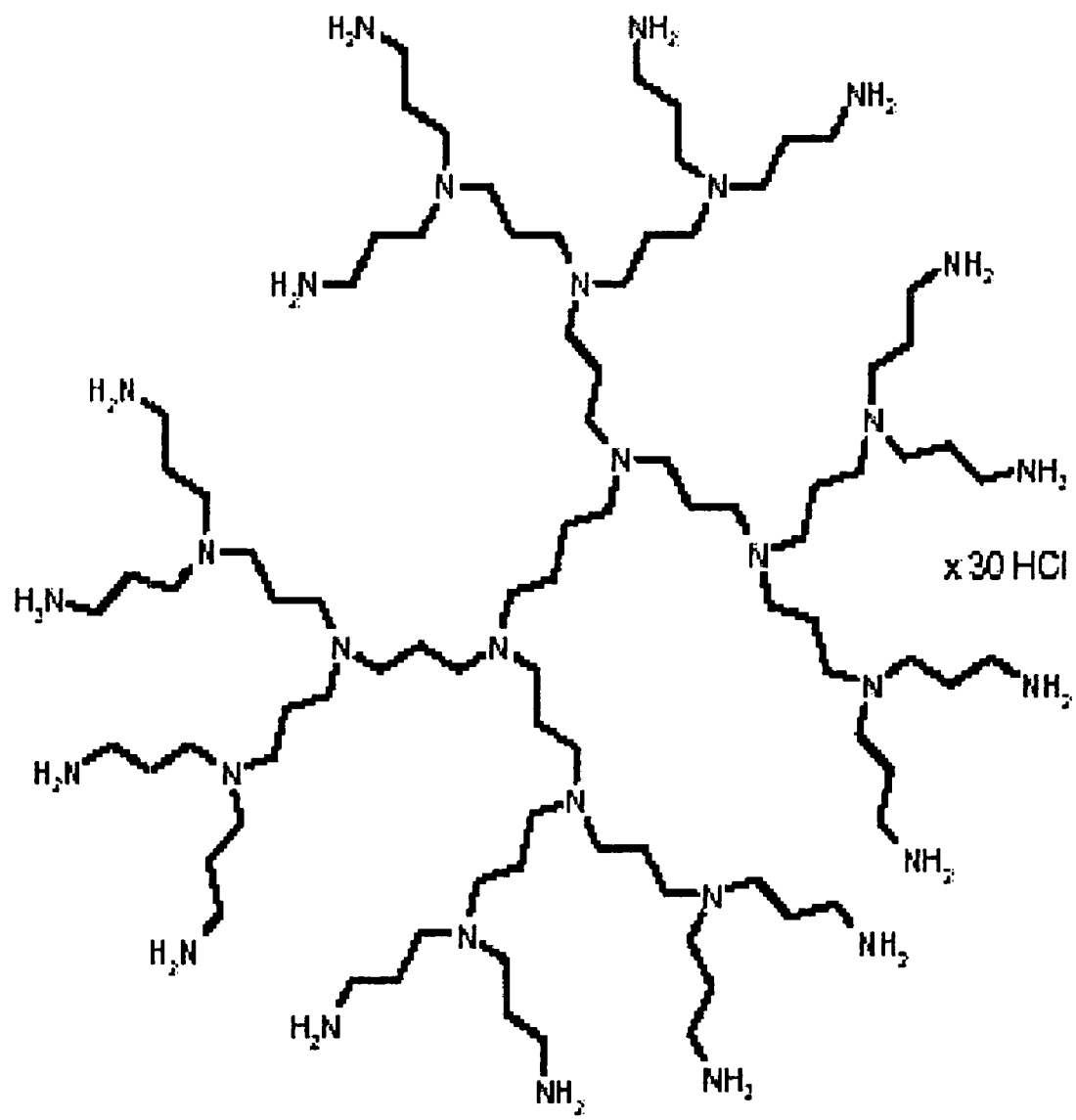
FIG. 1E) Structure 5: Diaminobutane dendrimer Generation 3 (DAB-16-Cl).
Figure 1F:
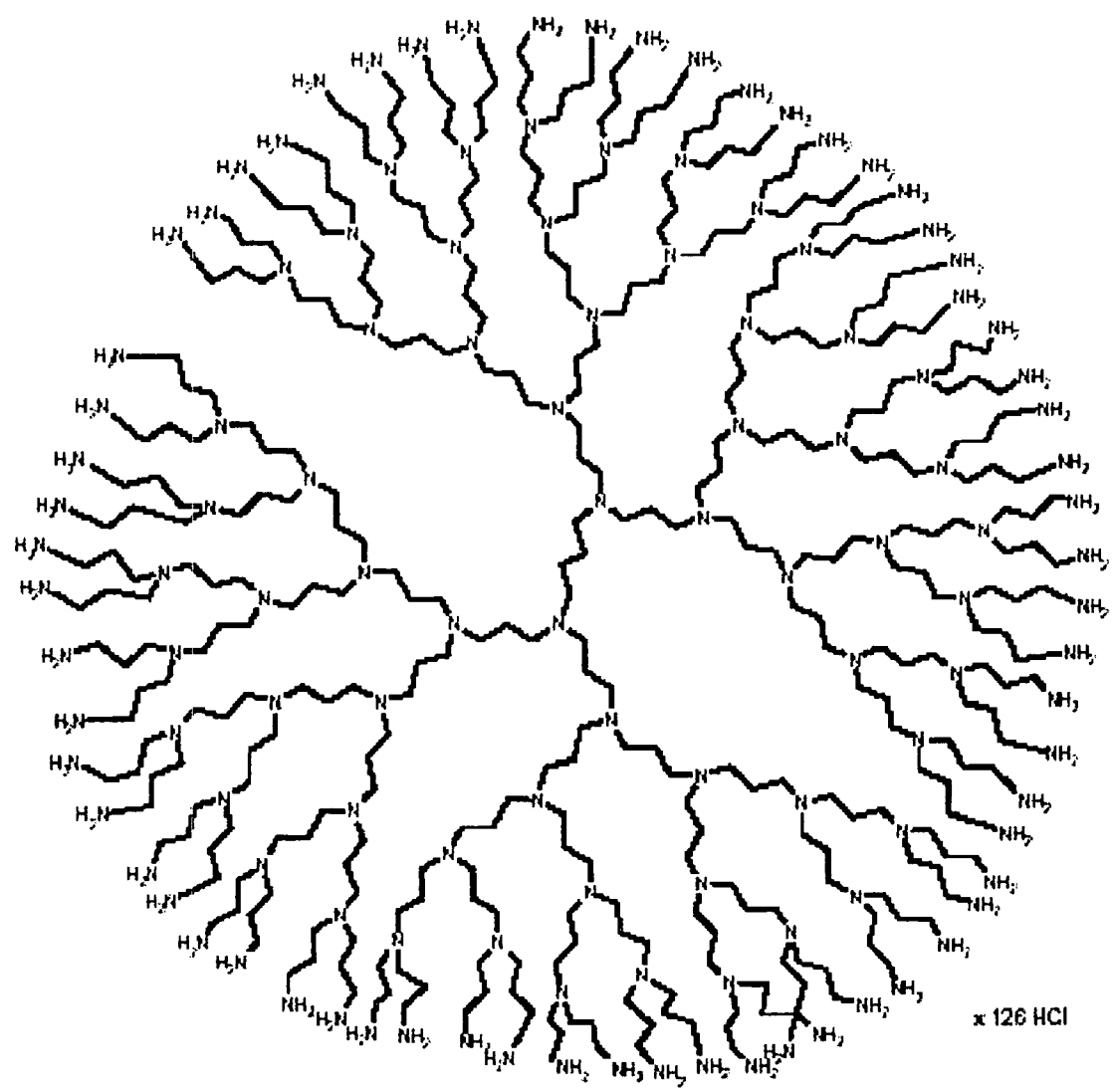
FIG. 1F) Structure 6: Diaminobutane dendrimer Generation 5 (DAB-64-Cl).
Figure 1G:
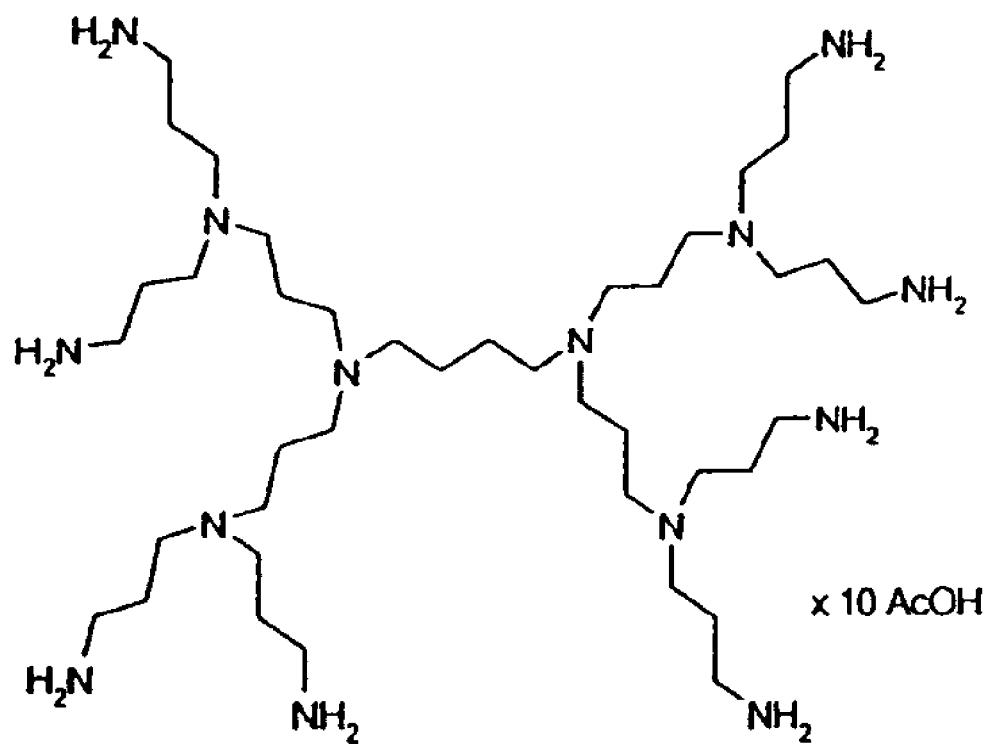
FIG. 1G) Structure 7: DAB-8-AcOH.

The present invention also provides therapeutic dendrimeric compositions. Preferably, the present invention is a hydrochloride, hydrobromide or hydroacetate form of dendrimers described in U.S. Pat. Nos. 5,530,092 and 5,610,268, incorporated herein. Most preferably, the present invention is the hydrochloride form of DAB-16 and DAB-64 (FIGS. 1E and 1F).

The present invention involves treating a patient with an amount of dendrimer composition effective to control serum phosphate levels in the patient. By "control," we mean increase and/or, more preferably, decrease the amount of phosphate absorbed by the patient's GI tract according to the dose and composition of the dendrimer administered to the patient. For instance, when a patient requires reduced levels of serum phosphate, the present invention prevents the absorption of substantial amounts of phosphate from the GI tract. By "substantial," we mean the present invention prevents at least 50% of phosphate from being absorbed in the GI tract. Most preferably, the present invention prevents at least 80% of the phosphate from being absorbed in the GI tract.

The effectiveness of this invention is determined by measuring the serum phosphate levels of the patient by any conventional test known to the art. The present invention is effective when the patient's serum phosphate levels are reduced by at least 10%, but more preferably, when the patient's serum phosphate levels are reduced by at least 20%.

The dendrimer is administered in an amount ranging between 2.5 and 15 grams per day. This dose is preferably equally divided among two or more meals. A preferable route of administration is in liquid form, such as a drink or a capsule. It is an advantage of the present invention that the dendrimer composition is soluble.

The invention also may include a pharmaceutical composition comprising a dendrimer composition combined with a pharmaceutically acceptable carrier intended to reduce and/or control serum phosphate levels in mammals. The composition may be administered to a mammal, a cell, or an isolated organ.

Examples of suitable pharmaceutical carriers are well known in the art and include phosphate buffered saline solutions, water, emulsions, such as oil/water emulsions, various types of wetting agents, sterile solutions and the like. Compositions comprising such carriers can be formulated by well known conventional methods. These pharmaceutical compositions can be administered to the mammal at a suitable dose.

Administration of the suitable compositions may be effected by different ways, e.g. by intravenous, intraperitoneal, subcutaneous, intramuscular, topical or intradermal injection, or by inhalation or intracranial injection.

By "dendrimer composition" we mean to include the molecules described in U.S. Pat. Nos. 5,530,092 and 5,610,268, incorporated by reference herein. These molecules include macromolecules comprising a core and branches emanating from the core, wherein the branches are based on vinyl cyanide and/or fumaryl dinatrile units. Most preferably, the dendrimer comprises a diaminobutane (DAB) dendrimer.

By "dendrimer composition" we also mean to include neutralized versions of dendrimers described in the patents listed above. Most preferably, the diaminobutane dendrimer is in the hydrochloride form, as described below. Other preferable neutralized forms include the hydrobromide (or any halide or organic acid) form and the hydroacetate form.

Dendrimer compositions of this kind may be synthesized according to conventional techniques, including those described in U.S. Pat. Nos. 5,530,092 and 5,610,268, incorporated by reference herein, and Buhleier, "Cascade" and "Non-skid-Chain-Like" Synthesis of Molecular Cavity Topologies, Synthesis, 155-158 (February 1978).

EXAMPLES

The following examples set forth preferred aspects of the present invention. It is to be understood, however, that these examples are provided by way of illustration and nothing therein should be taken as a limitation upon the overall scope of the invention.

Materials and Methods

Animals. Male Sprague-Dawley rats (Harlan Sprague-Dawley, Madison, Wis.) weighing approximately 120 grams were used in all experiments.

In experiments to measure $^{33}$P absorption, the rats were fed a laboratory chow diet (Lab Diet 5012, Richmond, Ind.) containing 1% calcium and 0.7% phosphorus ad libitum for less than one week prior to the experiment.

In experiments to measure fecal calcium and phosphorus levels, rats were fed purified diet described previously (9) for 9 days. This diet was mixed with egg white protein (Harlan Teklad, Madison, Wis.) and contained 0.20% inorganic phosphorus and 0.47% calcium. The purified diet was supplemented with 100 µL soybean oil (Wesson oil, ConAgra Foods, Irvine, Calif.) containing 500 µg α-tocopherol, 60 µg menadione, 40 µg β-carotene, and 1.875 µg cholecalciferol three times each week.

All rats were housed in hanging-wire cages under a 12-hour light/12-hour dark cycle and had free access to distilled water. All experimental methods were approved by the Research Animal Resources Center at the University of Wisconsin-Madison.

Intestinal Phosphate Absorption. Following an overnight fast, rats were administered 0.5 mL water or an oral phosphate binder dissolved in water via gastric gavage. A second dose of 0.5 mL containing 3 µCi $^{33}$P (as $H_3PO_4$, specific activity 155.8 Ci/mg, New England Nuclear/Perkin Elmer, Boston, Mass.) in a 10, 50, or 100 mM $KH_2PO_4$ buffer at pH 7.4 was immediately administered via gastric gavage. Rats were killed by $Co_2$ asphyxiation immediately or 60 minutes after the oral dose. The rats killed immediately (labeled "0 min control" in figures) were used to determine if the oral $^{33}$P dose was properly administered and completely recovered.

Blood was collected via heart puncture and centrifuged at 1500×g for 15 minutes at 22° C. to yield serum. A suture was tied to the cranial end of the esophagus to contain liquid inside the stomach. The entire digestive tract was then removed and allowed to dissolve for several days in concentrated $HNO_3$ (approximately 1 mL $HNO_3$ per gram tissue). The exact volume of the dissolved digestive tract was determined by diluting the dissolved tissues to equal volumes with water.

The amount of radioactivity in total body serum and total volume of dissolved tissue was determined following liquid scintillation counting of 50 µL aliquots in triplicate (Tri-Carb Liquid Scintillation Analyzer, Perkin-Elmer/Packard, Boston, Mass.). Total body serum was estimated to be 40 mL serum/kg body weight (10).

Fecal calcium and phosphorus measurements. Rats were fed the purified diet described above or the same diet with 1.2% calcium, 0.15% Renagel®, or 0.15% DAB4, DAB-8, or DAB-16 for 7 days. Rats were then moved to metabolic cages and fecal matter was collected for 48 hours. Fecal samples were frozen, lyophilized, and heated to over 600° C. overnight in a muffle oven. Remaining ash was then dissolved overnight in 25 mL 6 N HCl. The calcium concentration of the acid was determined by flame atomic absorption spectroscopy (Model 3110, Perkin Elmer, Norwalk, Conn.) using an aliquot of the dissolved ash diluted 1:40 with 1 g/L $LaCl_3$. The phosphorus concentration of an aliquot of the dissolved ash was determined by a colorimetric assay described previously (11).

Statistical analysis. Data are presented as means± standard error of the means (SEM). Treatment groups were compared by a fully factorial analysis of variance (ANOVA) and means were subjected to Tukey, Scheffe, and Fisher's Least-Significant-Difference (LSD) tests (Systat 5.2.1, Systat Software, Inc., Point Richmond, Calif.). Differences were considered significant if at least two of the tests detected significance with a p-value <0.05, unless specified otherwise.

Figure 6:
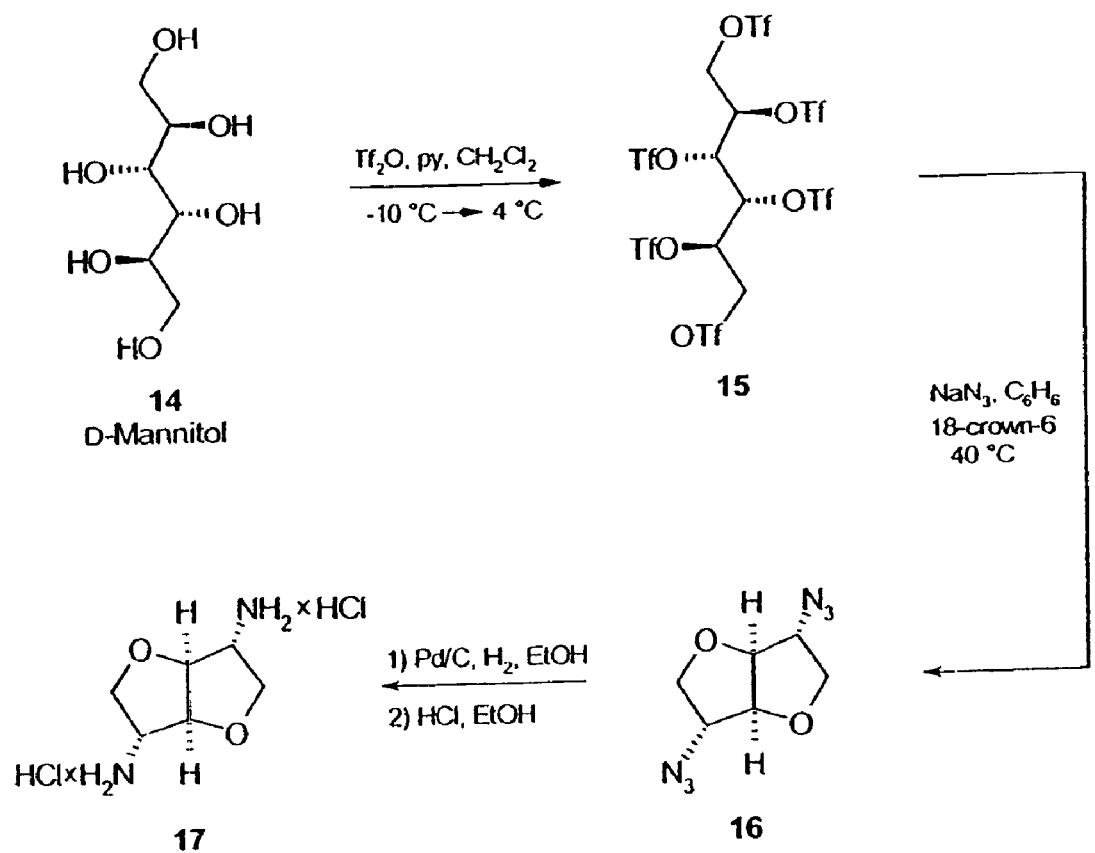
FIG. 6 illustrates the synthesis of Structure 1, FC.

Synthesis of Structure 1, FC. As seen in FIG. 6, the synthesis of Structure 1, FC (compound 17 in FIG. 6) is a three-step process. In step 1, a suspension of 174 mg (0.95 mmol) D-mannitol (compound 14) in 4 mL (49.4 mmol) dry pyridine was stirred under argon at room temperature for 0.5 h. Then, dry dichloromethane (14 mL) was added, the mixture was cooled down to −10° C. (salt-ice bath) and triflic anhydride (1.15 mL, 6.86 mmol) was added dropwise over a 0.5 h period. Stirring was continued at 4° C. (cold room) for 12 h. The solution was diluted with dichloromethane (20 mL) and washed with water (6×7 mL), saturated aqueous solution of $CuSO_4$ (7 mL), again water (3×7 mL) and dried over anhydrous $Na_2SO_4$, filtered. Evaporation of the solvents, then very fast column chromatography (30% hexane/ethyl acetate) afforded an unstable, creamy semisolid, compound 15 (139 mg, 0.14 mmol, 15% yield). [$α_D$]+97.9 (c.1.0, $CHCl_3$); $^1$H NMR (400 MHz, $CDCl_3$): δ 4.15 (m, 2H), 4.77 (dd, 2H, J=4.1 Hz, J=8.1 Hz), 5.21 (dd, 2H, J=4.3 Hz, J=9.3 Hz); $^{13}$C NMR (100 MHz, $CDCl_3$): δ 70.9, 80.4, 80.45,118.5 (q, $J_{C,F}$ = 318.98 Hz).

In step 2, 120 mg (0.123 mmol) compound 15 and 72 mg(1.107 mmol) NaN3 were dissolved in dry benzene (2 mL). The 18-crown-6 (0.956 g, 0.36 mmol) was added and the reaction mixture was stirred under argon at 40° C. for 3 h, then cooled down to room temperature, diluted with CH2CL2 (10 mL) and washed with water (6×4 mL). Organic layer was dried over anhydrous Na2SO4, filtered and very carefully concentrated under reduced pressure. The residue was purified by column chromatography (20% ethylacetate/hexane). After chromatography, solvents were removed under reduced pressure and finally by purging a stream of argon for 1 h to give compound 16 as a colorless oil (20 mg, 0.102 mmol, 83% yield). $^1$H NMR (400 MHz, $CDCl_3$): δ 3.89 (dd, 2H, J=4.0 Hz, J=10.2 Hz), 3.93 (dd, 2H, J=1.5 Hz, J=10.1 Hz), 4.6 (dd, 2H, J=1.2 Hz, J=3.8 Hz); $^{13}$C NMR (100 MHz, $CDCl_3$): δ 65.7, 71.9, 86.0.

In step 3, 20 mg (0.102 mmol) of compound 16 was dissolved in 2 mL ethanol and 10 mg of 10% Pd/C was added. Air was removed by purging with argon for 15 min. The mixture was hydrogenated using a slow stream of hydrogen at room temperature for 3 h (TLC control, 20% ethyl acetate/hexane). After that, the mixture was filtered through celite.

Flask and celite were washed with ethanol (10 mL). Filtrate containing crude 1,4:3,6-dianhydro-2,5-diamino-2,5-dideoxy-D-iditol was treated with a solution of HCl (aqueous HCl—37.3%: 35 μL, 0.432 mmol; ethanol: 1.2 mL) and stirred at room temperature for 2 h. Precipitate was then filtered off, washed with ethanol (15 mL), dried on air for 12 h and next in a vacuum oven at 60° C. for 48 h to give 13 mg (0.06 mmol, after two steps 59% yield) of compound 17 as a white crystal (m.p. above 270° C.; at 250° C. the compound turns dark grey. $[\alpha]_D$ +55.2 (c.1.1, $H_2O$); $^1H$ NMR (400 MHz, $D_2O$): δ 4.01-4.07 (m, 4H) 4.22 (dd, 2H, J=5.1 Hz, J=10.9 Hz), 5.01 (s, 2H);, J=1.5 Hz, J=10.1 Hz), $^1H$ NMR (400 MHz, DMSO-$d_6$): δ 3.68 (br s, 2H), 3.88 (dd, 2H, J=2.6 Hz, J=10.3 Hz), 3.98 (dd, 2H, J=5.2 Hz, J=10.4 Hz), 4.85 (s, 2H), 8.71 (br s, 6H); $^{13}C$ NMR (100 MHz, $D_2O$): δ 55.9, 70.1, 84.6; $^{13}C$ NMR (100 MHz, DMSO-$d_6$): δ 55.5, 70.2, 84.7; Elemental analysis calculated for $C_6H_{14}O_2N_2Cl_2$: C 33.52%, H 6.56%, N 13.03%, Cl 32.03%; found C 33.24%, H 6.43%, N 12.72%, Cl 33.98%.

Figure 7:
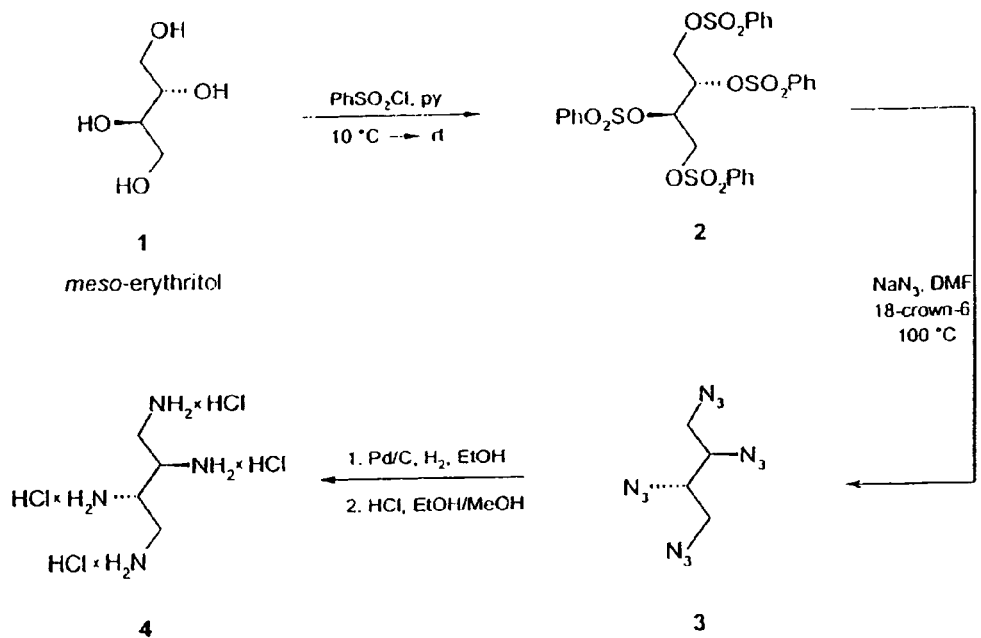
FIG. 7 illustrates the synthesis of Structure 2, KB-54.

Synthesis of Structure 2, KB-54. As seen in FIG. 7, the synthesis of Structure 2, KB-54 (compound 4 in FIG. 7) is a three-step process. Step 1 involves the synthesis of 1,2,3,4-Tetra-O-benzenesulfonyl-meso-erythritol (compound 2). Compound 3 is synthesized by dissolving 13 g (106 mmol) of meso-erythritol (compound 1) in dry pyridine (400 ml). The solution was cooled to −10° C. (salt ice bath) and benzenesulfonyl chloride (81.5 mL, 640 mmol) was added dropwise over a 1 h period. The cooling bath was removed and the mixture was stirred at room temperature for 5 h. The precipitate was collected and washed with ethyl acetate (250 ml), water (1L0 and again with ethyl acetate (200 ml). Then the product was dried with air for 12 h and then in vacuum oven at 50° C. for 30 h to yield 27 g (39 mmol, 37% yield) of white crystals (compound 2) (m.p. 184-186° C., lit. m.p. 184-185.5° C. -R. L. Willer, *J. Org. Chem.*, 1984, 49, 5150-5154). The organic filtrates were combined, concentrated to 200 mL and allowed to stand at room temperature to give the next portion of the crystalline product. Washing and drying procedures were repeated, yielding 30 g (44 mmol, 41% yield) of a second portion of compound 2 (m.p. 183-185° C.). Total yield was 57 g (83 mmol, 78% yield). $^1H$ NMR (400 MHz, $D_2O$): δ 4.03 (dd, 2H, J=6.6 Hz, J=11.5 Hz), 4.31 (d, 2H, J=11.5 Hz), 5.03 (d, 2H, J=6.7 Hz), 7.60-7.81 (m, 20H); $^{13}C$ NMR (100 MHz, DMSO-$d_6$): δ 66.7, 76.7, 127.56, 129.7, 129.8, 134.3, 134.6, 134.7, 134.8; MS (ESI) exact mass calculated for $C_{28}H_{26}O_{12}S_4Na([M+Na]^{30})$ 705.0205, found 705.175.

Step 2 involves the synthesis of erythro-1,2,3,4-tetraazidobutane (compound 3). This is accomplished by combining 27 g (39 mmol) of compound 2 with 17.17 g (264 mmol) $NaN_3$, 0.5 g (1.89 mmol) 18-crown-6 and 220 mL dry DMF in a flask equipped with a refluxing condenser. The reaction mixture was stirred at 100° C. for 48 h and then cooled to room temperature, diluted with water (0.5 L) and washed with $CH_2Cl_2$ (7×200 mL). Organic layers were combined, washed with water (8×100 mL) and saturated aqueous solution of NaCl (3×100 mL) dried over anhydrous $Na_2SO_4$, filtered and very carefully concentrated under reduced pressure. The dark brown residue (containing small amounts of DMF) was purified by column chromatograph (Hexane, 5-10% ethyl acetate/hexane) to give 6.36 g (0.028 mmol, 72% yield) of compound 3, a colorless liquid. Because of well known hazards of polyazido compounds, the product was partially concentrated under reduced pressure after chromatography and the residue of solvents was removed by purging a stream of argon for 2 h (R. L. Willer, *J. Org. Chem.*, 1984, 49, 5150-5154). $^1H$ NMR (400 MHz, $CDCl_3$): δ 3.52-3.8 (m, 4H) 3.67 (d, 2H, J=10.2 Hz); $^{13}C$ NMR (100 MHz, $CDCl_3$): δ 52.0, 61.5.

In step 3, 5.93 g (26.7 mmol) compound 3 was dissolved in 130 mL ethanol and 1.5 g 10% Pd/C was added. Air was removed by purging with argon for 15 min. The mixture was hydrogenated using a slow stream of hydrogen at room temperature for 5 h (TLC control, 10% ethylacetate/hexane). After that the mixture was filtered through celite. Flask and celite were washed with methanol (12 mL). Filtrate containing crude erythro-1,2,3,4-tetraamninobutane was treated with solution of HCl (aqueous HCl—36.3%: 9.73 ml, 117.4 mmol; methanol: 34 mL) and stirred at room temperature for 12 h. Pale pink precipitated was filtered off, washed with methanol (300 mL), dried on air for 12 h and then in vacuum oven at 60° C. for 48 h to give 4.84 g (8.3 mmol, after two steps, 68% yield) of compound 4 (m.p. 255° C.; at 150° C. compound 4 turns brown). $^1H$ NMR (400 MHz, $D_2O$): δ 3.20 (dd, 2H, J=8.6 Hz, J=14.0 Hz), 3.35(dd, 2H, J=3.0 Hz, J=14.0 Hz), 3.75 (br d, 2H, J=9.3 Hz); ; $^1H$ NMR (400 MHz, DMSO-$d_6$): δ 3.31 (dd, 2H, J=7.2 Hz, J=14.2 Hz), 3.47 (dd, 2H, J=3.8 Hz, J=14.3 Hz), 4.08 (br d, 2H, J=8.9 Hz), 8.98 (br s, 12H); $^{13}C$ NMR (100 MHz, $D_2O$): δ 39.0, 50.3; $^{13}C$ NMR (100 MHz, DMSO-$d_6$): δ 38.2, 49.9; Elemental analysis calculated for $C_4H_{18}N_4Cl_4$: C18.19%, H6.87%, N21.21%, Cl 53.71%; found C18.37%, H7.01%, N21.29%, Cl 53.46%.

Figure 8:
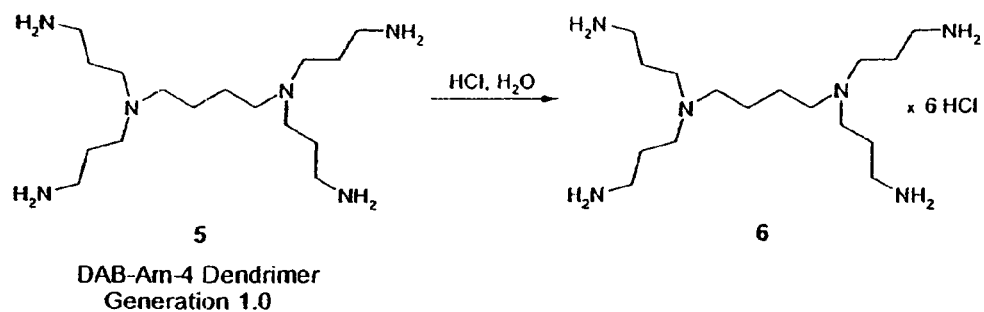
FIG. 8 illustrates the synthesis of Structure 3, DAB-4-Cl.

Synthesis of Structure 3, DAB4-Cl. As seen in FIG. 8, the conversion of DAB-Am-4 dendrimer into hydrochloride (compound 6) is accomplished by dissolving 8.47 g (26.76 mmol) of DAB-Am-4, Polypropylenimine tetraamine Dendrimer, Generation 1.0 (DSM product) (compound 5) in deionized water (200 mL). Air was removed by purging with argon for 15 min and solution of HCl (aqueous HCl—37.0%: 15.85 mL, 193.02 mmol; deionized water: 30 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (48 h) and finally in vacuum oven at 60° C. for 2 days to yield 14.32 g (26.75 mmol, quantitative yield) of beige crystal (compound 6) (m.p. 242-245° C.). $^1H$ NMR (400 MHz, $D_2O$): δ 1.89 (s, 4H), 2.14-2.24 (m, 8H), 3.15 (t, 8H, J=7.5 Hz), 3.36-3.40 (m, 12H); $^{13}C$ NMR (100 MHz, $D_2O$): δ 20.5, 21.6, 36.4, 49.9, 52.3; Elemental analysis calculated for $C_{16}H_{46}N_6Cl_6$: C 35.90%, H 8.66%, N 15.69%, Cl 39.73%; found C 35.88%, H 8.73%, N 15.28%, Cl 39.25%.

Figure 9:
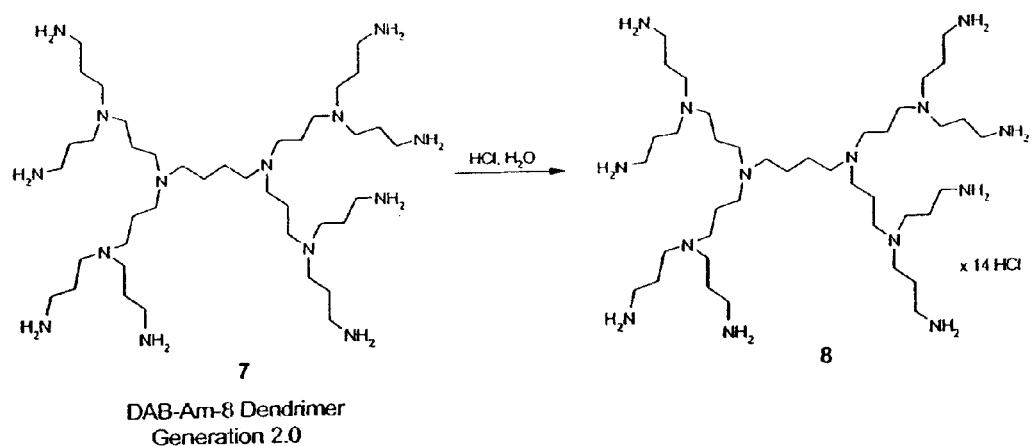
FIG. 9 illustrates the synthesis of Structure 4, DAB-8-Cl.

Synthesis of Structure 4, DAB-8-Cl. As seen in FIG. 9, the conversion of DAB-Am-8 Dendrimer, Generation 2.0 into hydrochloride (compound 8) is accomplished by dissolving (10 g, 12.93 mmol) of DAB-Am-8 Polypropylenimine octaamine Dendrimer, Generation 2.0 (DSM product) in deionized water (300 mL). Air was removed by purging with argon for 15 min and solution of HCl (aqueous HCl—37.0%: 19.3 mL, 235.44 mmol; deionized water: 40 mL) was added dropwise. Reaction mixture was stirred at room temperature for 1 h and then solvents were removed under reduced pressure. Residue was dissolved in 100 mL of deionized water and evaporated (procedure was repeated five times), dried on vacuum pump (24 h) and finally in vacuum oven at 60° C. for 3 days to yield 16.44 g (12.81 mmol, 99%) of white crystalline compound 8 (m.p. 153-155° C.). $^1H$ NMR (400 MHz, $D_2O$): δ 1.94 (s, 4H), 2.18-2.23 (m, 16H), 2.26-2.34 (m, 8H), 3.16 (t, 16H, J=7.8 Hz), 3.41-3.43 (m, 36H); $^{13}C$ NMR (100 MHz, $D_2O$): δ 19.0, 20.6, 21.6, 36.4, 49.8, 49.9, 50.0, 52.6; Elemental analysis calculated for $C_{40}H_{110}N_{14}Cl_{14}$: C 37.42%, H 8.63%, N 15.27%, Cl 38.66%; found C 35.81%, H 9.22%, N 14.52%, Cl 37.66%. Ratio of elements indicates full conversion of amino groups into hydrochlorides: calculated Cl/C 1.03, Cl/N 2.53, C/N 2.45; found Cl/C 1.05, Cl/N 2.59, C/N 2.46.

Figure 10:
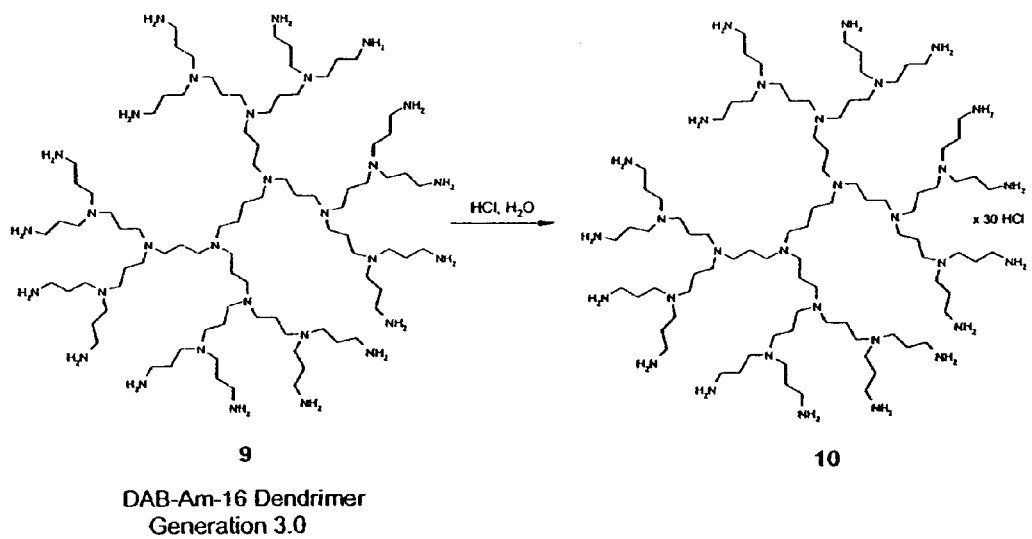
FIG. 10 illustrates the synthesis of Structure 5, DAB-16-Cl.

Synthesis of Structure 5, DAB-16-Cl. As seen in FIG. 10, the conversion of DAB-Am-16 dendrimer, Generation 3.0 into hydrochloride (10) is accomplished by dissolving 5 g (2.96 mmol) DAB-Am-16 dendrimer, polypropylenimine hexadecaamine dendrimer (9) in deionized water (150 mL). Air was removed by purging with argon for 15min and HCl solution (aqueous HCl—37%: 9.5mL, 115.56 mmol deionized water: 20 mL) was added dropwise. Reaction mixture was stirred at room temperature for 1 h and then solvents were removed under reduced pressure. Residue was dissolved in 150 mL deionized water and evaporated (procedure was repeated five times), dried on vacuum pump (24 h) and finally in vacuum oven at 60° C. for 3 days to yield 8.24 g (2.96 mmol, quantitative yield) of creamy crystalline compound (10) (m.p. 266° C.). $^{1}$H NMR (600MHz, D$_2$O): δ 1.81 (s, 4H), 2.07-2.10 (m, 32H), 2.14-2.19 (m, 24H), 3.06(t, 32H, J=7.7 Hz), 3.28-2.37 (m, 84H); $^{13}$C NMR (100 MHz, D$_2$): δ 19.0, 19.1, 20.7, 21.6, 36.4, 49.8, 49.9, 50.1, 50.3, 52.9; Elemental analysis calculated for C$_{88}$H$_{238}$N$_{30}$Cl$_{30}$: C 38.01%, H 8.63%, N 15.11%, Cl 38.25%; found C 38.25%, H 9.13%, N 15.11%, Cl 38.25%. Ratio of elements indicates full conversion of amino groups into hydrochlorides: calculated Cl/C 1.01, Cl/N 2.53, C/N 2.51; found Cl/C 1.03, Cl/N 2.60, C/N 2.52.

Figure 11:
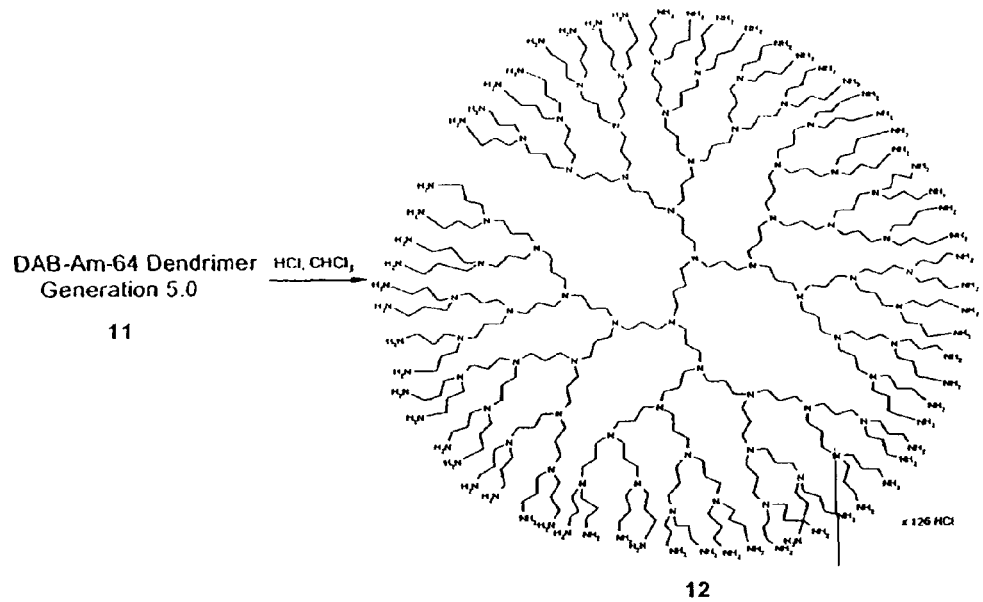
FIG. 11 illustrates the synthesis of Structure 6, DAB-64-Cl.

Synthesis of Structure 6, DAB-64-Cl. As seen in FIG. 11, the conversion of DAB-Am-64 dendrimer, Generation 5.0 into hydrochloride (12) is accomplished by dissolving 1.06 g (0.14 mmol) of DAB-Am-64, polypropylenimine tetrahexacontaamine dendrimers in CH$_3$Cl (25 mL). Air was removed by purging with argon for 15 min and concentrated solution of HCl (aqueous HCl—37.3%: 1.66 mL, 19.99 mmol) was added dropwise. Reaction mixture was stirred at room temperature for 1 h and then solvents were removed under reduced pressure. The residue was dissolved in 20 mL of deionized water and evaporated (procedure was repeated five times), dried on vacuum pump (5 h) and finally in vacuum oven at 60° C. for 3 days to yield 1.525 g (0.13 mmol, 95% yield) of yellow crystalline compound (12) (m.p. 274-276° C.). $^{1}$H NMR (600 MHz, D$_2$O): δ 1.793 (s, 4H), 2.11-2.19 and 2.23-2.34 (2×m, 248H), 3.09 (t, 128H, J=7.6 Hz), 2.32-2.47 (m, 372H); $^{13}$C NMR (100 MHz, D$_2$O)-only easy visible signals: δ 19.2, 19.3, 20.9, 21.8, 36.7, 49.3, 49.7, 49.9, 50.3, 51.0; Elemental analysis calculated for C$_{376}$H$_{1006}$N$_{126}$Cl$_{126}$: C 38.39%, H 8.62%, N 15.00%, Cl 37.97%; found C 38.43%, H 9.25%, N 15.05%, Cl 38.35%. Ratio of elements indicates full conversion of amino groups into hydrochlorides: calculated Cl/C 0.99, Cl/N 2.53, C/N 2.55; found Cl/C 0.99, Cl/N 2.54, C/N 2.55.

Figure 12:
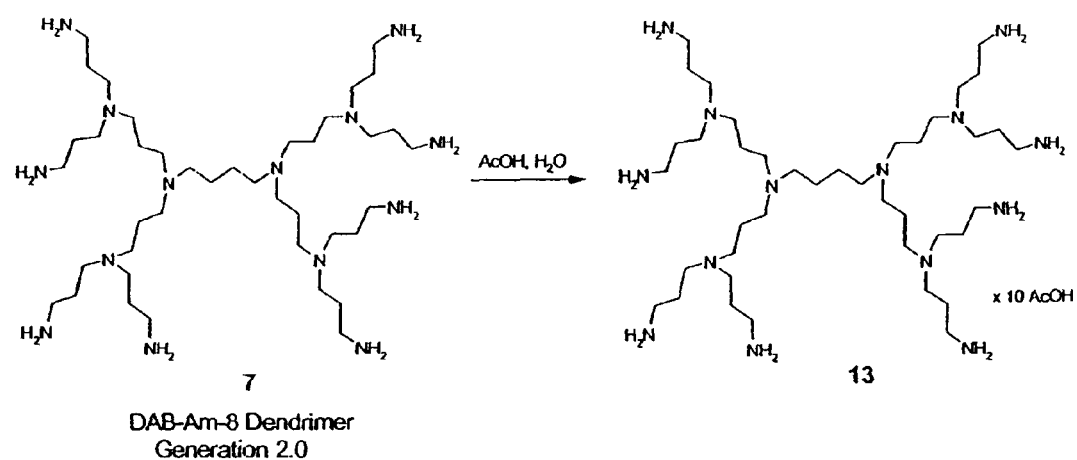
FIG. 12 illustrates the synthesis of Structure 7, DAB-8-AcOH.

Synthesis of Structure 7, DAB-8-AcOH. As seen in FIG. 12, the conversion of DAB-Am-8 dendrimer, Generation 2.0 into decahydroacetate is accomplished by dissolving 6.92 g (8.95 mmol) of DAB-Am-8, Polypropylenimine octaamine Dendrimer, Generation 2.0 (DSM product) 1 in deionized water (260 mL). Air was removed by purging with argon for 15 min and solution of AcOH (glacial AcOH: 8.0 mL, 137.86 mmol; deionized water: 160 mL) was added dropwise. Reaction mixture was stirred at room temperature for 12 h and then solvents were removed under reduced pressure. Residue was dissolved in 250 mL of deionized water and evaporated (procedure was repeated sixteen times). Finally sample was dissolved in 100 mL of deionized water, frozen and lyophilized (48 h) to yield 11.78 g (8.57 mmol, 96%) of compound 3 as the very sticky pale orange oil. $^{1}$H NMR (400 MHz, D$_2$O): δ 1.63 (s, 4H), 1.74-1.85 (m, 24H), 1.88 (s, 30 H), 2.52-2.62 (m, 24H), 2.86-3.02 (m, 28H); $^{13}$C NMR (100 MHz, D$_2$O): δ 20.9, 21.7, 23.2, 23.4, 37.7, 49.7, 50.3, 50.8, 52.6, 181.3; Elemental analysis calculated for C$_{60}$H$_{136}$N$_{14}$O$_{20}$: C 52.45%, H 9.97%, N 14.27%; found C 52.05%, H 10.28%, N 14.43%.

Results

Calcium or Renagel® bind phosphate in vivo. In previous measurements of intestinal phosphate absorption, $^{33}$P was administered in a 0.5 mM KH$_2$PO$_4$ buffer. However, when 0.5 mM KH$_2$PO$_4$ was mixed with 100 mM CaCl$_2$, that concentration of phosphate did not precipitate. This suggests that a higher concentration of KH$_2$PO$_4$ is needed for calcium to bind phosphate. In fact, to detect precipitation of phosphate by excess calcium, the level of phosphate needed to be raised to 10 mM (data not shown). Thus, to determine optimal conditions for testing oral phosphate binders in vivo, water, 20 mg calcium (as calcium acetate), or 14.4 mg Renagel® were administered to fasted rats. Rats were immediately administered an oral dose of $^{33}$P in a buffer containing 10, 50, or 100 mM KH$_2$PO$_4$ and killed after 60 minutes.

Figure 2:
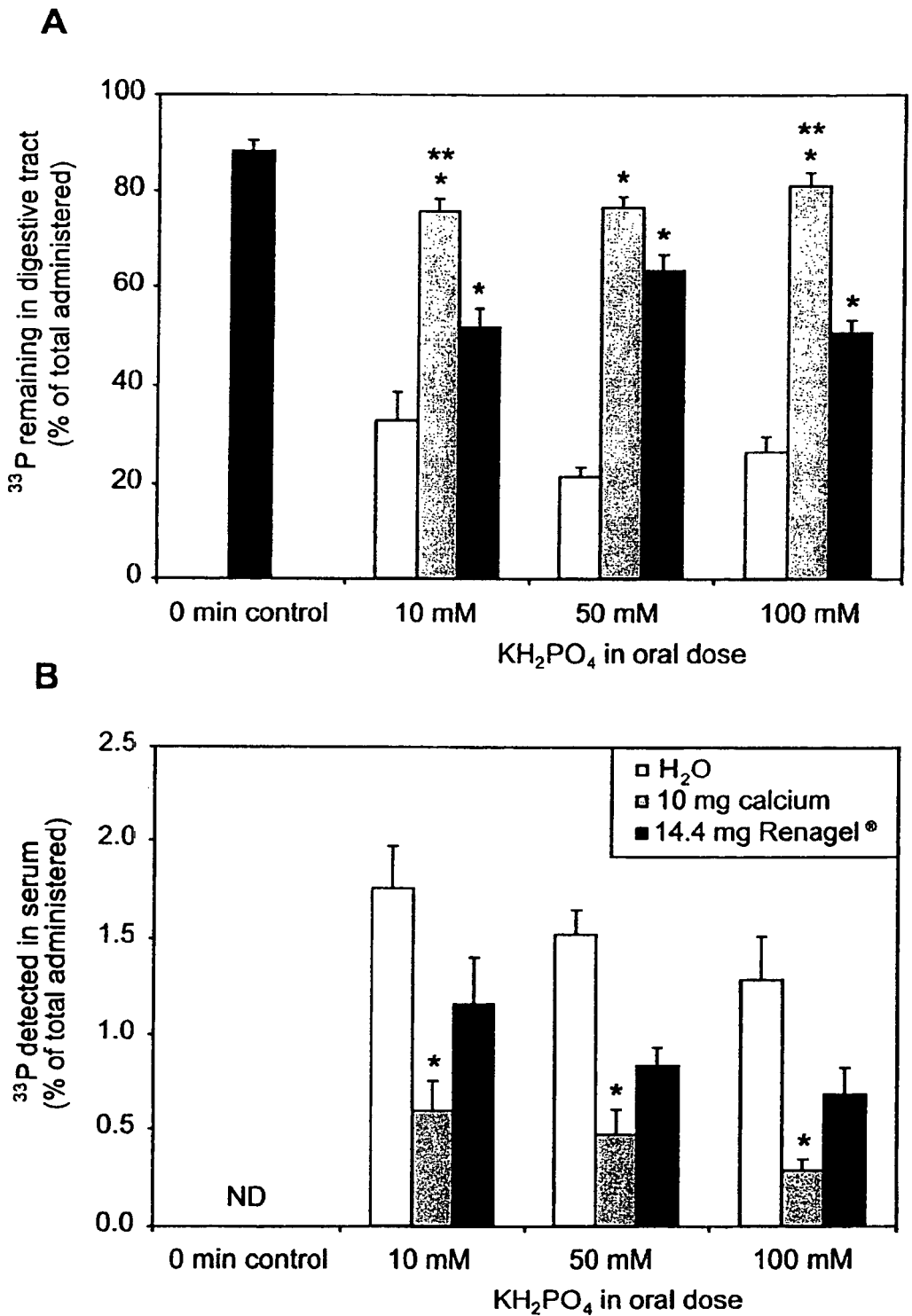
FIG. 2 shows that Calcium or Renagel® bind phosphate in vivo. Fasted rats were administered 0.5 mL water or 20 mg calcium (as calcium acetate) or 14.4 mg Renagel® dissolved in water via gastric gavage. Rats were immediately administered a dose of 3 µCi $^{33}$P in 0.5 mL buffer containing 10, 50, or 100 mM $KH_2PO_4$, and killed after 60 minutes.
Figure 3:
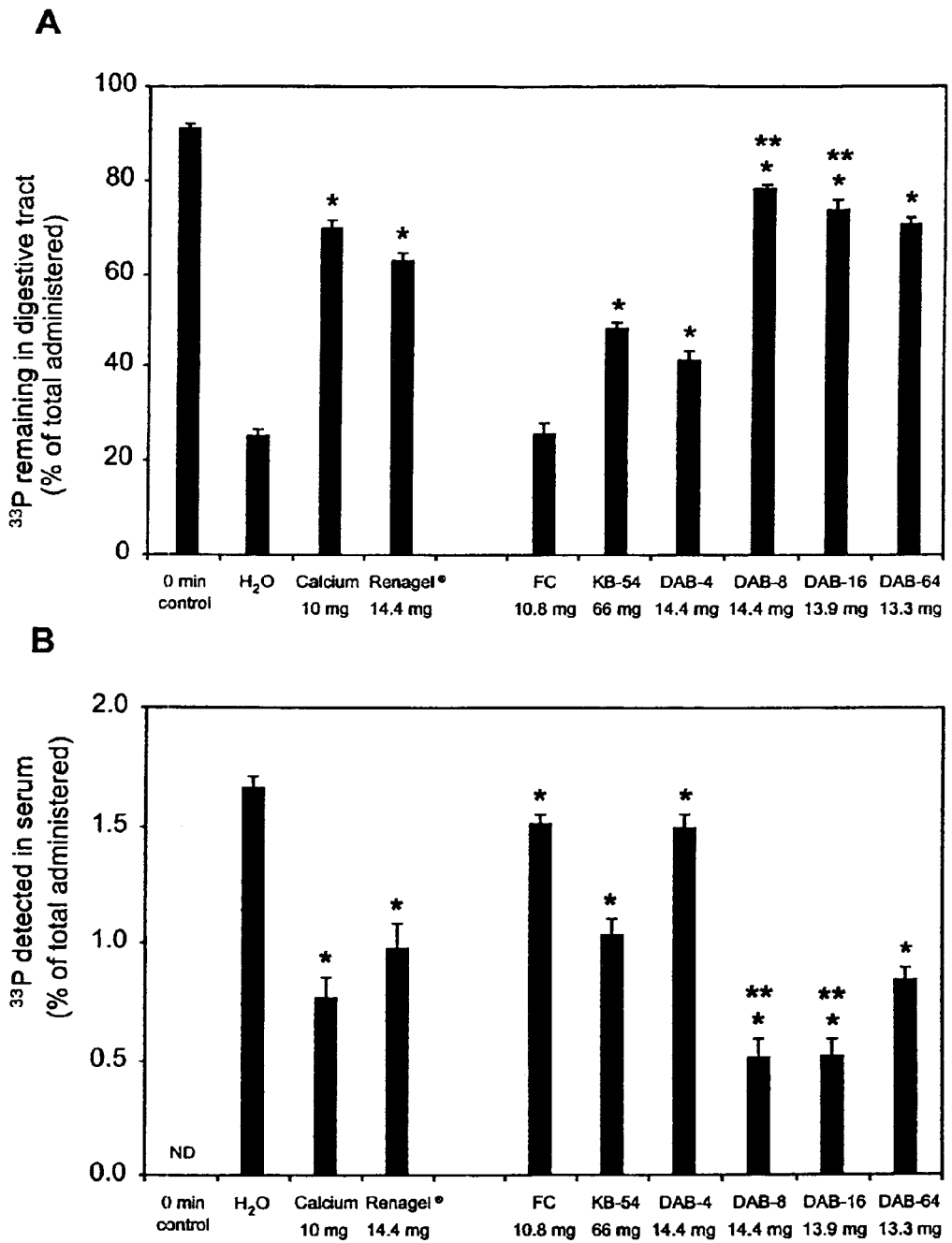
FIG. 3 compares the novel oral phosphate binders disclosed herein. Fasted rats were administered 0.5 mL water or 10 mg calcium (as calcium acetate), 14.4 mg Renagel®, or a novel phosphate binder (described in Table 1) dissolved in water via gastric gavage. Rats were immediately administered a second dose of 3 µCi $^{33}$P in 0.5 mL buffer containing 10 mM $KH_2PO_4$, and killed after 60 minutes.

As shown in FIG. 2A, rats administered 20 mg calcium or 14.4 mg Renagel® prior to $^{33}$P had significantly more $^{33}$P remaining in the intestine after 60 minutes than rats administered water prior to $^{33}$P regardless of the level of unlabeled phosphate in the oral dose. Moreover, 20 mg calcium bound more $^{33}$P in the intestine than did 14.4 mg Renagel®, and this difference reached significance when $^{33}$P was administered in 10 or 100 mM phosphate. A significant decrease in serum $^{33}$P levels was also detected in rats dosed with 10 mg calcium, but the decrease in serum $^{33}$P levels observed in rats dosed with 14.4 mg Renagel® was not statistically significant (FIG. 2B).

Figure 4:
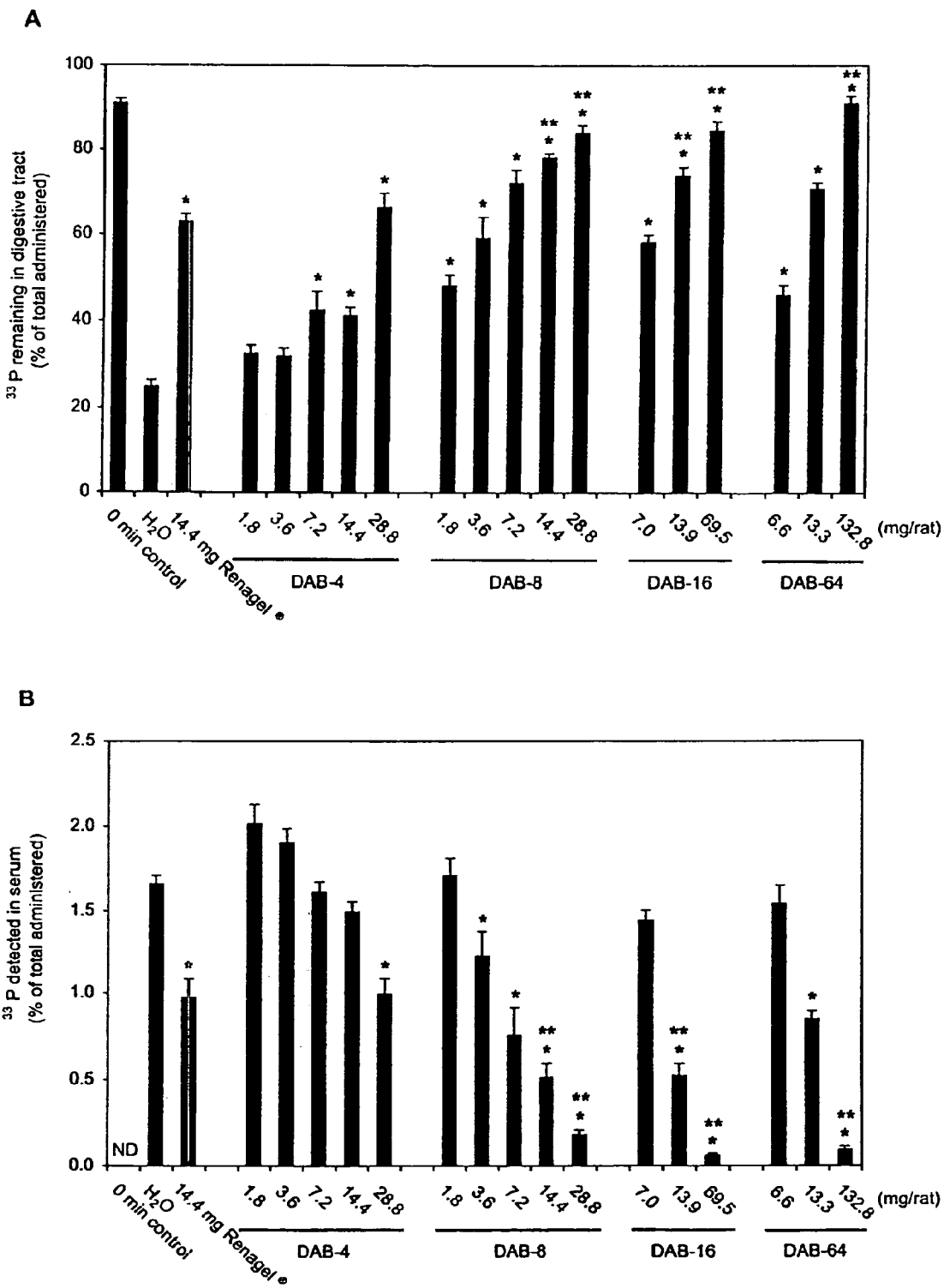
FIG. 4 illustrates the dose response to dendrimer compounds. Fasted rats were administered 0.5 mL water or 14.4 mg Renagel® or a novel phosphate binder dissolved in water via gastric gavage. Rats were immediately administered a dose of 3 µCi $^{33}$P in 0.5 mL buffer containing 10 mM $KH_2PO_4$, and killed after 60 minutes.

Comparison of novel oral phosphate binders. The binding ability of novel oral phosphate binders shown in FIG. 1 was compared to calcium and Renagel®. Table 1 lists the weight and molar amounts of all compounds used in this and subsequent experiments. Rats were first administered 0.5 mL water or 0.5 mL water containing 10 mg calcium (as calcium acetate), 14.4 mg Renagel®, or a novel phosphate binder. An oral dose of $^{33}$P in a 10 mM KH$_2$PO$_4$ buffer was immediately administered and rats were killed after 60 minutes. Both 10 mg calcium and 14.4 mg Renagel® significantly increased the amount of $^{33}$P remaining in the digestive tract (FIG. 4A), and significantly reduced serum $^{33}$P levels (FIG. 4B).

The novel binders KB-54 (Structure 2, FIG. 1B), DAB-4 (Structure 3, FIG. 1C), DAB-8 (Structure 4, FIG. 1D), DAB-16 (Structure 5, FIG. 1E) and DAB-64 (Structure 6, FIG. 1F) also significantly increased the amount of $^{33}$P remaining in the digestive tract and significantly reduced serum $^{33}$P levels. Furthermore, DAB-8-Cl (Structure 4, FIG. 1D) and DAB-16-Cl (Structure 5, FIG. 1E) significantly increased the amount of $^{33}$P remaining in the digestive tract and significantly reduced serum $^{33}$P levels compared to a comparable amount of Renagel®. FC (Structure 1, FIG. 1A) did not affect the amount of $^{33}$P that remained in the digestive tract, but caused a slight, but significant, decrease in serum $^{33}$P levels.

TABLE 1

Summary of solutions used to bind oral $^{33}$P dose. 0.5 mL of solution containing an oral phosphate binder was administered to rats prior to the oral $^{33}$P dose. NA = not available because structural information is proprietary.

| Oral phosphate binder | mg/rat | moles/Liter (M) | Moles NH$_2$/Liter |
|---|---|---|---|
| Calcium acetate | 10 | 0.5 | 0 |
| Renagel ® | 14.4 | NA | NA |
| FC | 10.8 | 0.1 | 0.2 |
| KB-54 | 66 | 0.5 | 1.0 |
| DAB-4 | 1.8 | 0.00675 | 0.027 |
|  | 3.6 | 0.0135 | 0.054 |
|  | 7.2 | 0.027 | 0.108 |
|  | 10.7 | 0.04 | 0.160 |
|  | 14.4 | 0.054 | 0.216 |
|  | 28.8 | 0.108 | 0.432 |
| DAB-8 | 1.8 | 0.0028 | 0.0224 |
|  | 3.6 | 0.0056 | 0.0448 |
|  | 7.2 | 0.01 | 0.08 |
|  | 10.7 | 0.011 | 0.088 |
|  | 14.4 | 0.022 | 0.176 |
|  | 28.8 | 0.045 | 0.36 |
| DAB-16 | 6.95 | 0.005 | 0.08 |
|  | 13.9 | 0.01 | 0.16 |
|  | 69.5 | 0.05 | 0.8 |
| DAB-64 | 6.64 | 0.00115 | 0.0736 |
|  | 13.28 | 0.0023 | 0.1472 |
|  | 132.8 | 0.023 | 1.472 |

Dose response to dendrimer compounds. The ability of DAB-4, DAB-8, DAB-16, and DAB-64 to bind phosphate was compared in a dose response study. Rats were first administered 0.5 mL water, 0.5 mL water containing 14.4 mg Renagel®, or a dendrimer. An oral dose of $^{33}$P in a 10 mM $KH_2PO_4$ buffer was immediately administered and rats were killed after 60 minutes. All dendrimer compounds increased $^{33}$P remaining in the digestive tract (FIG. 4A) and correspondingly decreased serum $^{33}$P (FIG. 4B) levels in a dose-dependent manner.

Nearly all the increases in $^{33}$P remaining in the digestive tract, and many of the decreases in serum $^{33}$P levels, were statistically significant. In addition, the two highest levels of DAB-8 and DAB-16, and the highest level of DAB-64, significantly increased $^{33}$P remaining in the intestine and significantly reduced serum $^{33}$P levels compared to Renagel®.

Mechanism underlying the dendrimer compound's ability to bind phosphate. To determine if the number of free amino groups in the dendrimer compound is responsible for its phosphate binding ability, rats were administered equal numbers of moles or free amino groups from DAB-4, DAB-8 and DAB-16. Rats were immediately administered an oral dose of $^{33}$P in a 10 mM $KH_2PO_4$ buffer and killed after 60 minutes.

Figure 5:
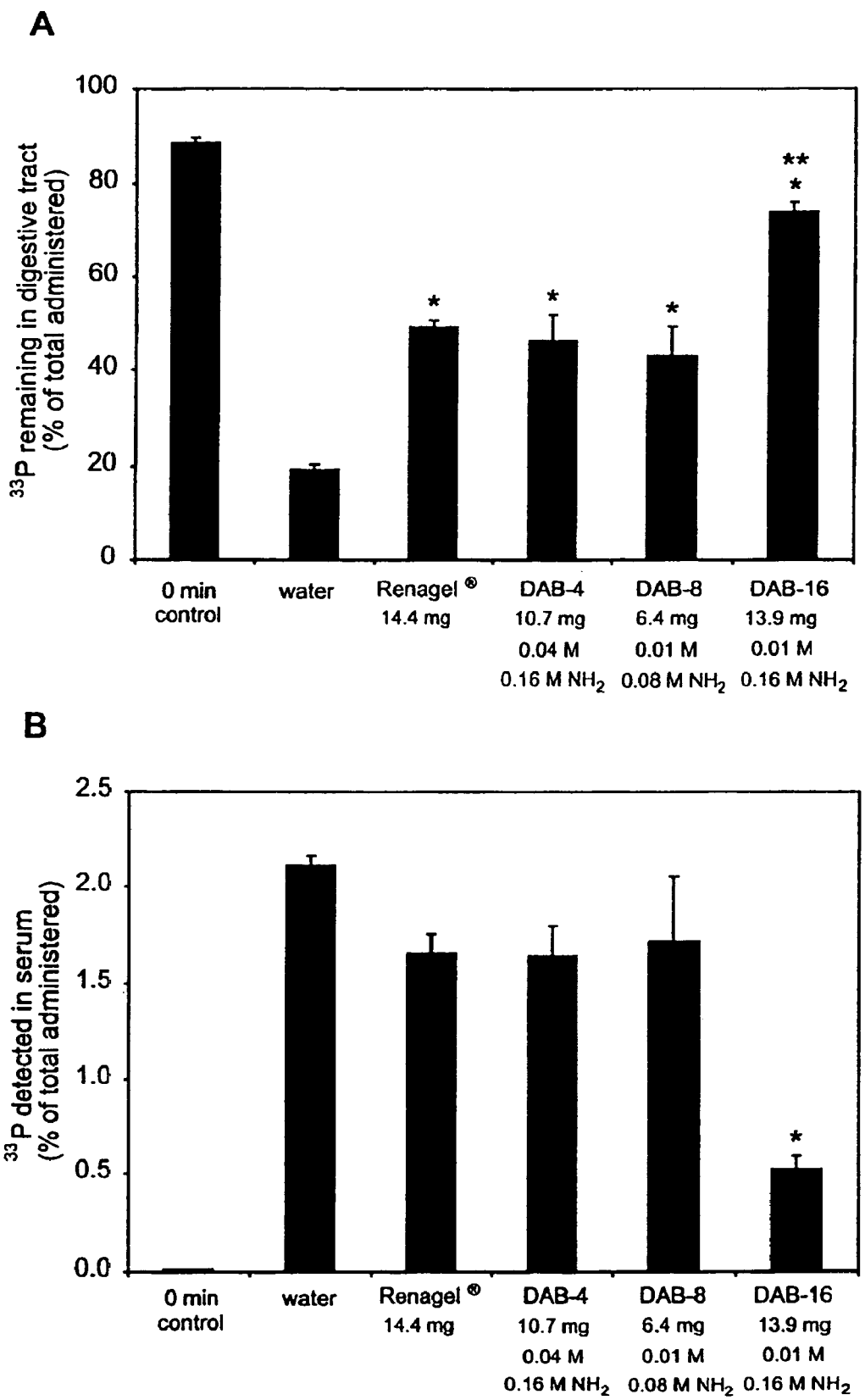
FIG. 5 illustrates the mechanism underlying the dendrimer's ability to bind phosphate. Fasted rats were administered 0.5 mL water or 14.4 mg Renagel® or a novel phosphate binder dissolved in water via gastric gavage. Rats were immediately administered a dose of 3 µCi $^{33}$P in 0.5 mL buffer containing 10 mM $KH_2PO_4$, and killed after 60 minutes.

As seen in FIG. 5A, Renagel® and all levels of the dendrimers were able to increase the amount of $^{33}$P remaining in the digestive tract to a significant degree. However, 13.9 mg DAB-16-Cl was the only level of binder able to significantly reduce serum $^{33}$P levels (FIG. 5B). Interestingly, when an equivalent amount of free amino groups were added from DAB4 and DAB-16, DAB-16 was able to retain significantly more $^{33}$P in the digestive tract. In addition, when equimolar amounts of DAB-8-Cl and DAB-16-Cl were administered to rats, DAB-16-Cl retained significantly more $^{33}$P in the digestive tract.

Rats were fed a purified control diet containing 0.47% calcium and 0.20% phosphorus or the same diet with added calcium, or 0.15% Renagel®, DAB-4, DAB-8, or DAB-16 for one week. Fecal samples were then collected for 48 hours, dried, and ashed. Ash was dissolved in acid to determine calcium and phosphorus levels. Fecal calcium levels were significantly increased in rats fed a 1.20% calcium diet, confirming that diets were mixed and administered correctly. Fecal phosphorus was increased, though not significantly, in rats fed a diet containing 1.20% calcium or 0.15% DAB-4. As shown in Table 2, rats fed 0.15% DAB-8 or DAB-16 had significantly increased fecal phosphorus levels compared to rats fed a control diet or a diet with 0.15% Renagel® according to Fisher's LSD test only.

Figure 13:
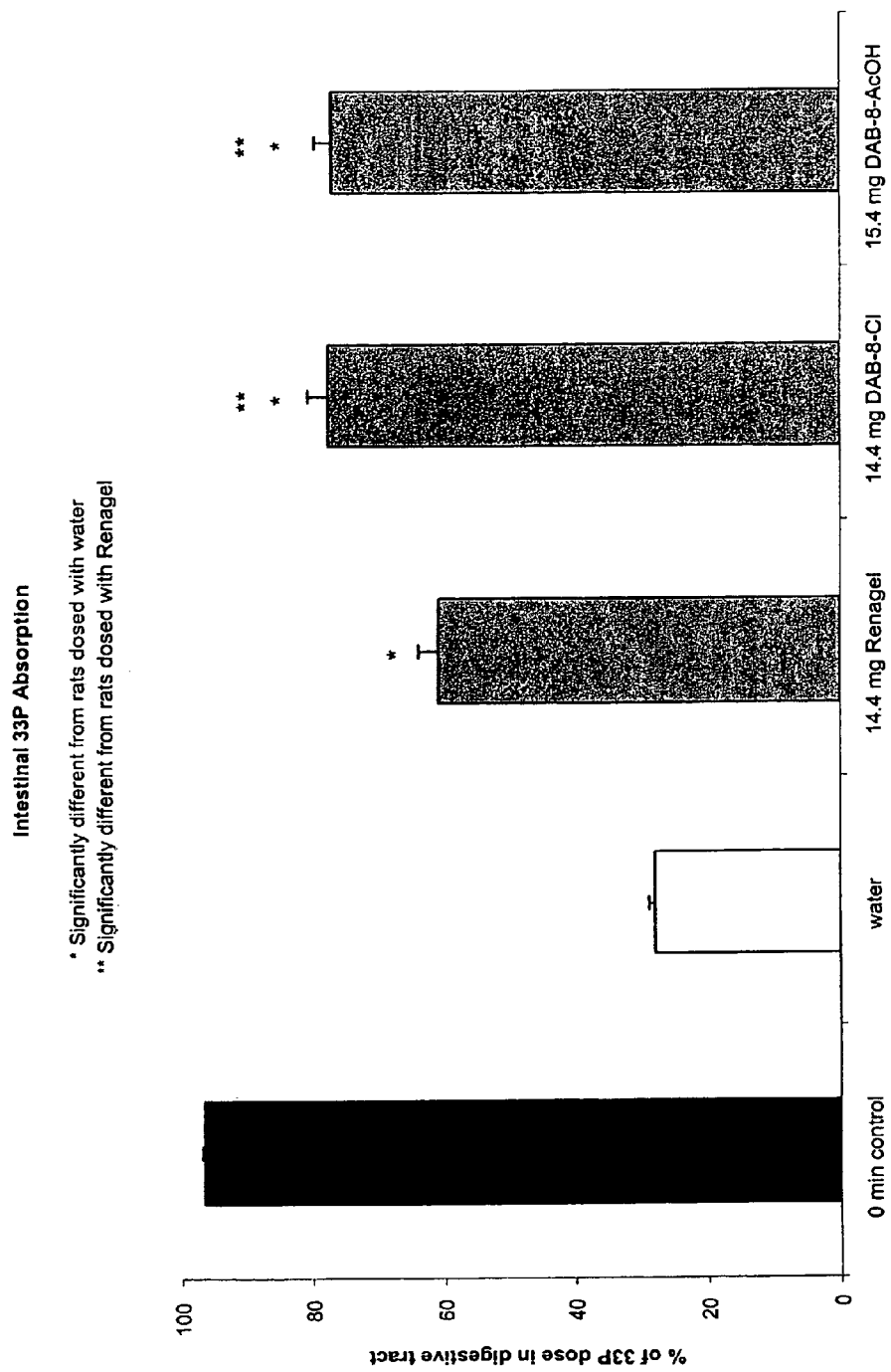
FIG. 13 illustrates the effect of hydroacetate dendrimers on intestinal $^{33}$P absorption.
Figure 14:
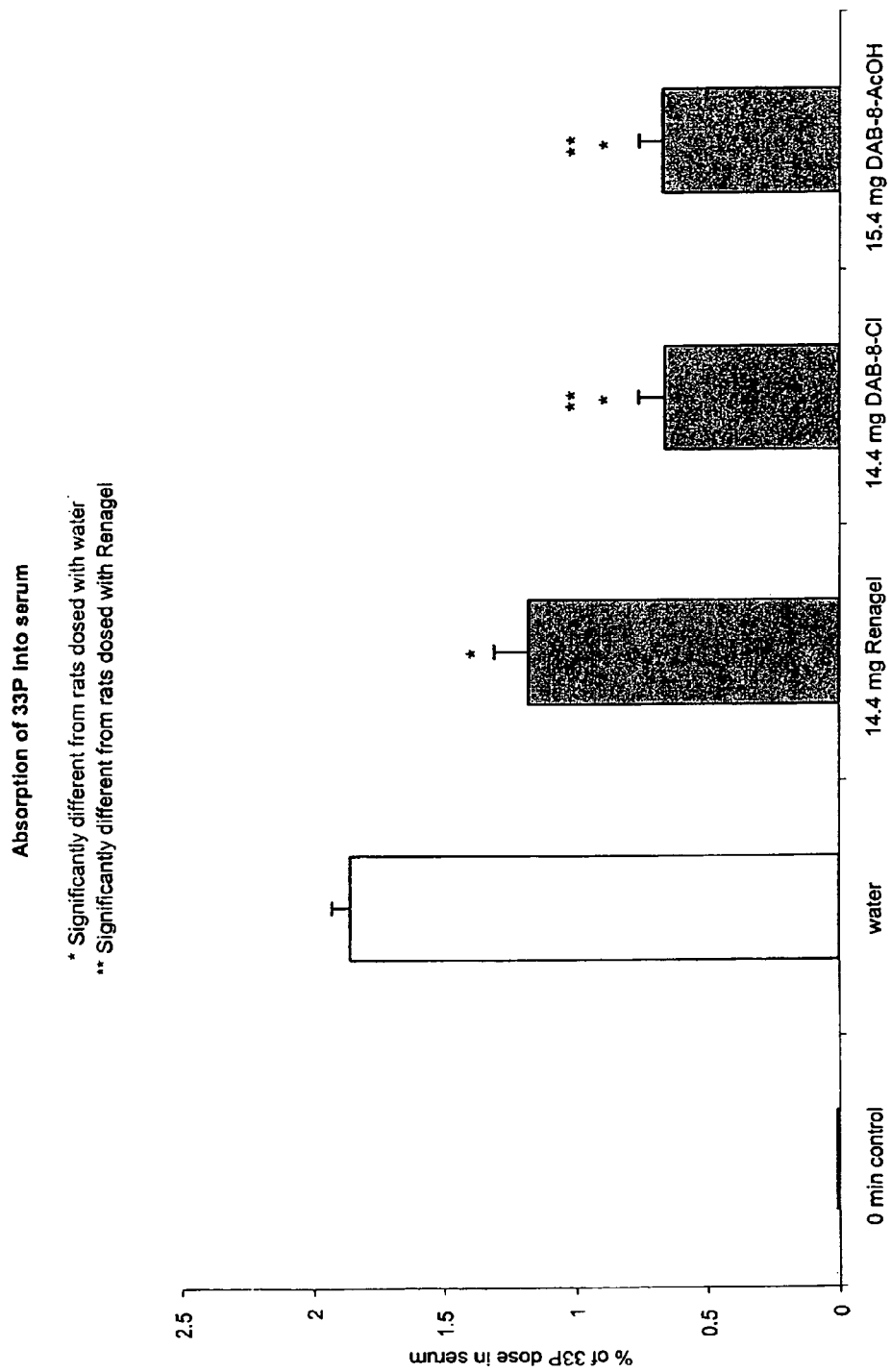
FIG. 14 illustrates the effect of hydroacetate dendrimers on absorption of $^{33}$P into serum.

As seen in FIGS. 13 and 14, hydroacetete dendrimers (such as structure 7, FIG. 1G) work just as effectively as the hydrochloride dendrimers.

TABLE 2

Dendrimers increase fecal phosphorus levels. Fecal calcium and phosphorus levels from rats fed a control diet containing 0.47% Ca and 0.2% P, or control diet with added calcium, Renagel ®, DAB-4, DAB-8, or DAB-16. Data are presented as means ± standard error of the means (SEM). * Significantly different from amount of calcium in feces from rats fed control diet (p < 0.05). ** Significantly different from amount of calcium in feces from rats fed control diet as detected by Fisher's LSD test only (p < 0.05).

| Group | mg Ca per gram feces | mg P per gram feces |
|---|---|---|
| Control | 11.23 ± 0.84 | 3.79 ± 0.18 |
| 1.20% Ca | 80.71 ± 4.60 * | 4.39 ± 0.23 |
| 0.15% Renagel ® | 13.06 ± 1.08 | 3.69 ± 0.21 |
| 0.15% DAB-4 | 14.28 ± 2.01 | 4.30 ± 0.13 |
| 0.15% DAB-8 | 16.06 ± 1.44 | 4.71 ± 0.53 ** |
| 0.15% DAB-16 | 15.82 ± 1.52 | 4.78 ± 0.30 ** |

Conclusion

Managing blood phosphate is a challenging, but essential, element in the treatment of secondary hyperparathyroidism in chronic kidney disease patients. In addition to dialysis treatment, patients are often administered vitamin D analogs to suppress PTH levels and oral phosphate binders to reduce the absorption of phosphate from foods. Although several types of oral phosphate binders have been developed, all have limited effectiveness due to potential toxicity, low binding ability, or high cost.

The present document compares a variety of novel compounds containing free amino groups for the potential to bind phosphate when administered orally in rats. One of these compounds, FC, does not appear to bind an oral $^{33}$P dose. However, KB-54 and the first, second, third and fifth generations of a DAB dendrimer reduced the absorption of an oral $^{33}$P dose. Each generation of the dendrimer compound bound oral $^{33}$P in a dose dependent manner, and DAB-8 and DAB-16 bound significantly more $^{33}$P than did an equivalent amount of Renagel®.

The mechanism by which dendrimer compounds bind phosphate was investigated by measuring the ability of equal number of moles and equal number of free amino groups from DAB-4, DAB-8, and DAB-16 to reduce the absorption of $^{33}$P. When an equivalent number of free amino groups was administered in the form of DAB-4 and DAB-16, DAB-16 bound significantly more $^{33}$P, suggesting free amino groups are not exclusively responsible for the dendrimer's ability to bind phosphate. However, when an equimolar amount of DAB-8 and DAB-16 were administered to rats, DAB-16 retained significantly more $^{33}$P in the digestive tract, implying that the number of free amino groups may be, in part, responsible for the dendrimer compound's ability to bind phosphate.

Tolerable levels of the DAB-4, DAB-8, and DAB-16 dendrimers were then fed to rats and were found to increase fecal phosphorus levels. Although the differences were significant by the Fisher's LSD test only, the increase in fecal phosphorus by DAB-8 and DAB-16 was significantly higher then the increase from excess calcium or an equivalent amount of Renagel®.

Unfortunately, little is known regarding the toxicity of DAB dendrimers when administered orally. Previous research has shown DAB dendrimers to be cytotoxic in vitro (12), and when administered intravenously, the DAB dendrimers are lethal (13). In our experiments, however, the DAB dendrimers were well tolerated by rats when administered orally. DAB-4, DAB-8, and DAB-16 as hydrochlorides were tolerated at 0.15% of the diet, but when fed at levels as high as 0.3% or 0.6%, only softened stool was observed after 5 days (data not shown).

REFERENCES

1. Brown, A. J., Dusso, A. S., and Slatopolsky, E. 2002. Vitamin D analogues for secondary hyperparathyroidism. Nephrol Dial Transplant 17 Suppl 10: 10-19.
2. Food and Nutrition Board, Institute of Medicine. 1997. Dietary reference intakes for calcium, phosphorus, magnesium, vitamin D, and fluoride. Washington, D.C.: National Academy Press.
3. Wardlaw, G. M., and Kessel, M. W. 2002. Perspectives in Nutrition. New York, N.Y.: McGraw-Hill Higher Education.
4. Tenenhouse, H. S. 2005. Regulation of phosphorus homeostasis by the Type IIa Na/phosphate cotransporter. Annu Rev Nutr 25:197-214.
5. Goodman, W. G. 2003. Medical management of secondary hyperparathyroidism in chronic renal failure. Nephrol Dial Transplant 18 Suppl 3:III2-8.
6. Coladonato, J. A. 2005. Control of hyperphosphatemia among patients with ESRD. J Am Soc Nephrol 16 Suppl 2:S107-114.

7. Amin, N. 2002. The impact of improved phosphorus control: use of sevelamer hydrochloride in patients with chronic renal failure. Nephrol Dial Transplant 17:340-345.
8. Cizman, B. 2003. Hyperphosphataemia and treatment with sevelamer in haemodialysis patients. Nephrol Dial Transplant 18 Suppl 5:vb 47-49.
9. Suda, T., DeLuca, H. F., and Tanaka, Y. 1970. Biological activity of 25-hydroxyergocalciferol in rats. J Nutr 100: 1049-1052.
10. Hawk, T., and Leary, S. L. 1999. Formulary for laboratory animals. Ames, Iowa: Iowa State University Press.
11. Itaya, K., and Ui, M. 1966. A new micromethod for the colorimetric determination of inorganic phosphate. Clin Chim Acta 14:361-366.
12. Duncan, R., and Izzo, L. 2005. Dendrimer biocompatibility and toxicity. Adv Drug Deliv Rev 57:2215-2237.
13. Schatzlein, A. G., Zinselmeyer, B. H., Elouzi, A., Dufes, C., Chim, Y. T., Roberts, C. J., Davies, M. C., Munro, A., Gray, A. I., and Uchegbu, I. F. 2005. Preferential liver gene expression with polypropylenimine dendrimers. J Control Release 101:247-258.
14. Svenson, S., Tomalia, D. A. 2005. Dendrimers in biomedical applications-reflections on the field. Advanced Drug Delivery Reviews 57:2106-2129.

We claim:

1. A method of controlling serum phosphate levels in mammals comprising administering to the mammal an amount of a diaminobutane dendrimer selected from the group consisting of

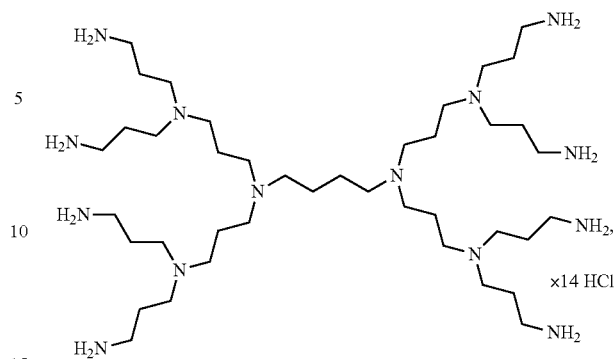

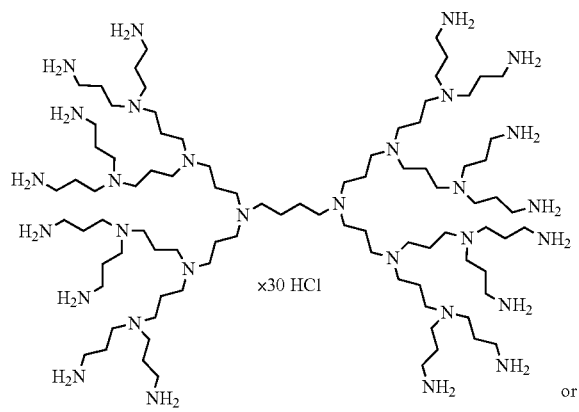

or

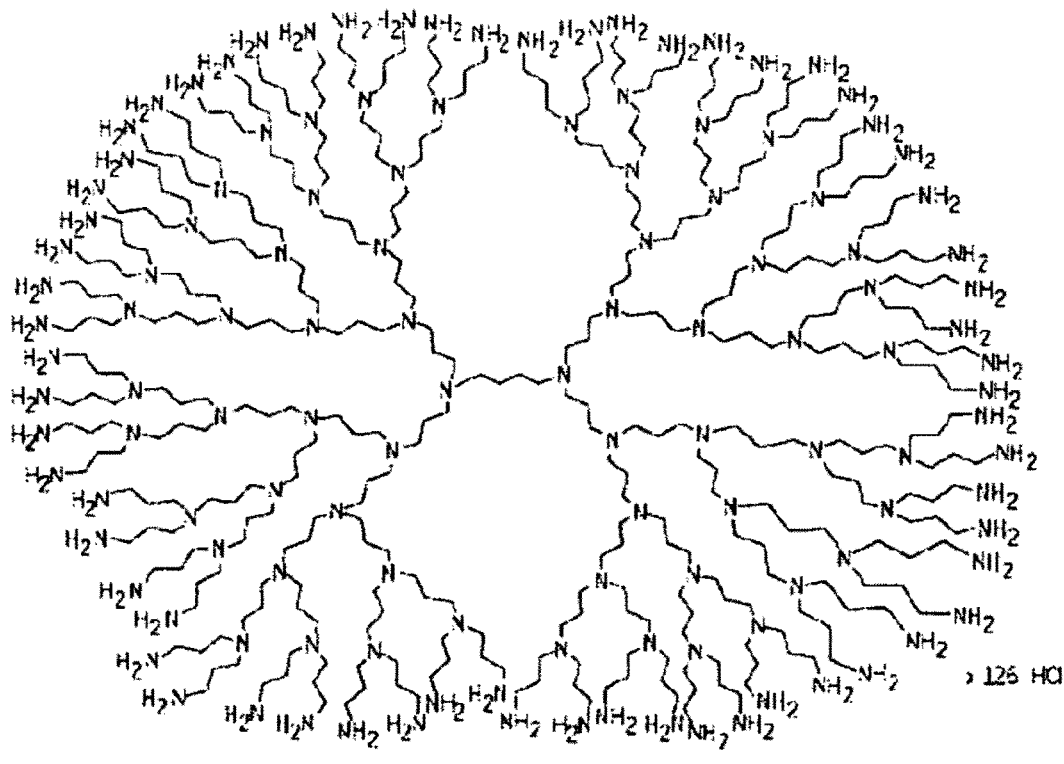

, effective to prevent absorption of substantial amounts of phosphate from the mammal's GI tract, wherein at least 50% of phosphate in the mammal's GI tract is prevented from being absorbed, and the mammal's serum phosphate level is controlled.

2. The method of claim 1 wherein at least 80% of phosphate in the mammal's GI tract is prevented from being absorbed.

3. The method of claim 1 wherein the amount of dendrimer composition administered to the mammal is between 2.5 and 15 grams per day.

4. A method of reducing intestinal phosphate absorption in animals by administering to the animal an amount of a diaminobutane dendrimer selected from the group consisting of

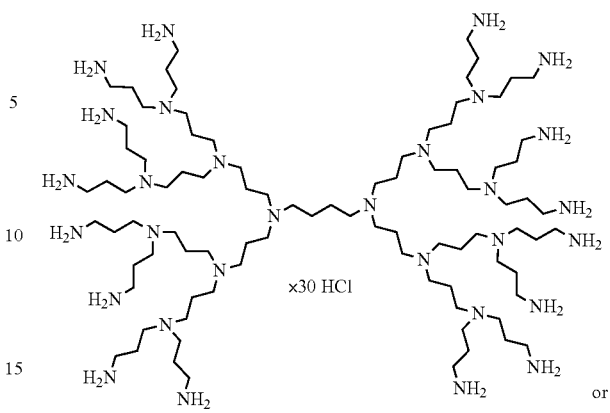

or

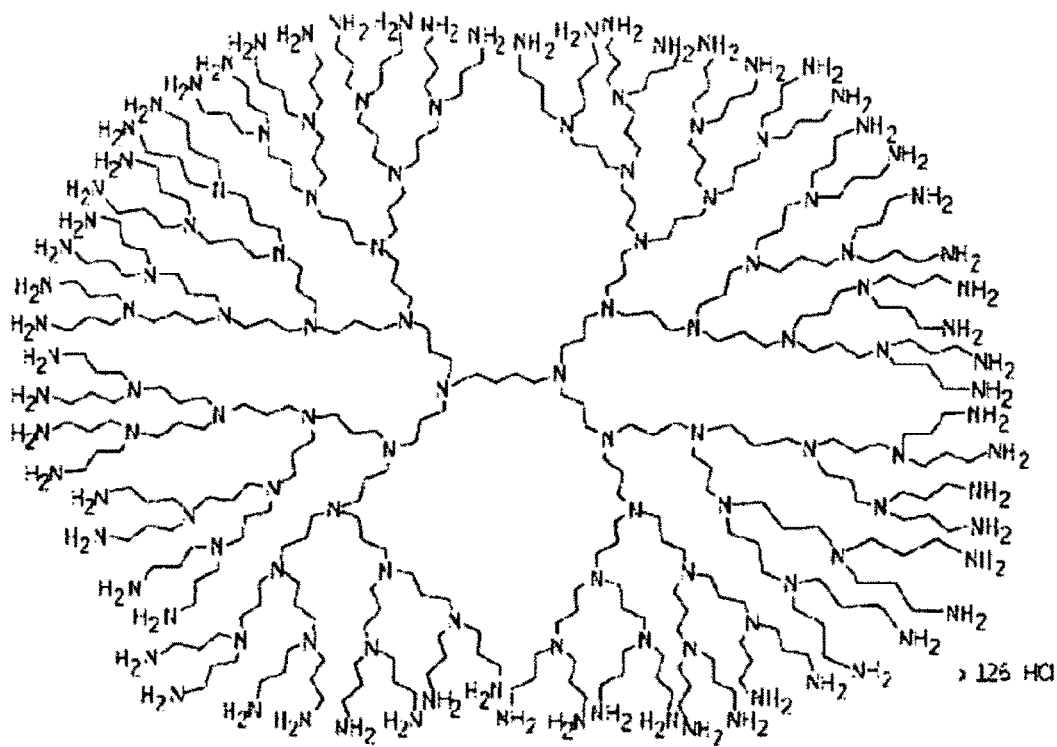

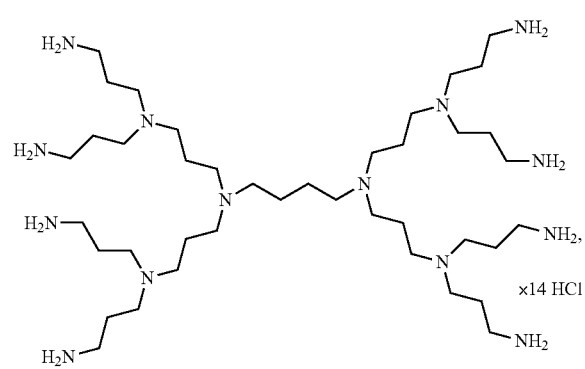

effective to prevent absorption of substantial amounts of phosphate from the animal's GI tract, wherein at least 50% of phosphate in the mammal's GI tract is prevented from being absorbed, and the animal's intestinal phosphate absorption is reduced.

5. The method of claim 4 wherein at least 80% of phosphate in the animal's GI tract is prevented from being absorbed.

6. The method of claim 4 wherein the amount of dendrimer composition administered to the animal is between 2.5 and 15 grams per day.

* * * * *

UNITED STATES PATENT AND TRADEMARK OFFICE
CERTIFICATE OF CORRECTION

PATENT NO. : 8,158,117 B2
APPLICATION NO. : 11/520389
DATED : April 17, 2012
INVENTOR(S) : DeLuca et al.

It is certified that error appears in the above-identified patent and that said Letters Patent is hereby corrected as shown below:

Column 7, line 45 "$[M+Na]^{30}$" should read -- $[M+Na]^+$ --

Column 8, line 5 "tetraamninobutane" should read -- tetraaminobutane --

Column 9, line 10 "$D_2$):" should read -- $D_2O$: --

Column 11, line 61, Table 2 "1.20% Ca" should read -- 1.20% coil array --

Signed and Sealed this
Thirty-first Day of July, 2012

David J. Kappos
*Director of the United States Patent and Trademark Office*